US009708379B2

(12) United States Patent
Lin et al.

(10) Patent No.: US 9,708,379 B2
(45) Date of Patent: Jul. 18, 2017

(54) COMPOSITIONS FOR REGULATING IRON HOMEOSTASIS AND METHODS OF USING SAME

(75) Inventors: Herbert Y. Lin, Watertown, MA (US); Jodie L. Babitt, Newton Highlands, MA (US); Tracey Menhall, Boston, MA (US); Patrick Gearing, North Seattle, WA (US)

(73) Assignees: THE GENERAL HOSPITAL CORPORATION, Boston, MA (US); FERRUMAX CORPORATION, Boston, MA (US)

( * ) Notice: Subject to any disclaimer, the term of this patent is extended or adjusted under 35 U.S.C. 154(b) by 462 days.

(21) Appl. No.: 13/980,666

(22) PCT Filed: Jan. 19, 2012

(86) PCT No.: PCT/US2012/021829
§ 371 (c)(1),
(2), (4) Date: Feb. 25, 2014

(87) PCT Pub. No.: WO2012/150973
PCT Pub. Date: Nov. 8, 2012

(65) Prior Publication Data
US 2014/0199302 A1  Jul. 17, 2014

Related U.S. Application Data

(60) Provisional application No. 61/434,405, filed on Jan. 19, 2011.

(51) Int. Cl.
| | |
|---|---|
| *C07K 14/705* | (2006.01) |
| *C07K 14/47* | (2006.01) |
| *C07K 14/71* | (2006.01) |
| *C12N 15/62* | (2006.01) |
| *C07K 16/24* | (2006.01) |
| *A61K 38/17* | (2006.01) |

(52) U.S. Cl.
CPC ........ *C07K 14/4703* (2013.01); *C07K 14/71* (2013.01); *C07K 16/24* (2013.01); *C12N 15/62* (2013.01); *A61K 38/179* (2013.01); *C07K 2319/21* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 5,731,168 | A * | 3/1998 | Carter .............. | C07K 14/70514 435/69.1 |
| 7,511,018 | B2 * | 3/2009 | Goldberg ............... | A61K 38/40 435/183 |
| 7,968,091 | B2 * | 6/2011 | Woolf ................ | A61K 38/1709 424/134.1 |
| 8,637,023 | B2 * | 1/2014 | Lin ..................... | A61K 38/1709 424/134.1 |
| 8,895,002 | B2 * | 11/2014 | Lin ....................... | C07K 14/71 424/134.1 |
| 2007/0004618 | A1 | 1/2007 | Ganz et al. | |
| 2012/0164140 | A1 | 6/2012 | Lin et al. | |

FOREIGN PATENT DOCUMENTS

| | | | | |
|---|---|---|---|---|
| DE | WO 2009030500 A1 * | 3/2009 | .......... | C07K 14/705 |
| EP | 1 862 555 A1 | 12/2007 | | |
| JP | 2009-522329 A | 6/2009 | | |
| JP | 2009-536968 A | 10/2009 | | |
| WO | 0118172 A2 | 3/2001 | | |
| WO | WO 2006/088972 | 8/2006 | | |
| WO | 2007/077173 A1 | 7/2007 | | |
| WO | 2007/134147 A2 | 11/2007 | | |
| WO | 2008124768 A1 | 10/2008 | | |
| WO | WO 2008124768 A1 * | 10/2008 | ............ | C07K 14/71 |
| WO | 2009074637 A1 | 6/2009 | | |
| WO | 2009152944 A1 | 12/2009 | | |

OTHER PUBLICATIONS

Genbank printout for human Hemojuvelin downloaded Mar. 11, 2016, accession No. Q6ZVN8, from ncbi.nlm.nih.gov/protein/q6zvn8, 10 pages.*
Pinnix et al., Sci Transl Med. Aug. 4, 2010;2(43):43ra56. doi: 10.1126/scisignal.3001127.*
Chen et al., Blood. Jun. 9, 2011;117(23):6319-25. doi: 10.1182/blood-2010-12-327957. Epub Apr. 14, 2011.*
O'Connor, JP., Semin Cell Dev Biol. Oct. 4, 2016. pii: S1084-9521(16)30315-9. doi: 10.1016/j.semcdb.2016.10.001. [Epub ahead of print].*
International Preliminary Report on Patentability, International Application No. PCT/US2012/021829, Korean Intellectual Property Office, Jul. 23, 2013.
International Search Report and Written Opinion, International Application No. PCT/US2012/021829, Korean Intellectual Property Office, Sep. 19, 2012.
Andriopoulos, et al., (2009), "BMP6 is a key endogenous regulator of hepcidin expression and iron metabolism," Nature Genetics, 41(4):482-487.
Nili, et al., (2010), "Soluble repulsive guidance molecule c/hemojuvelin is a broad spectrum bone morphogenetic protein (BMP) antagonist and inhibits both BMP2- and BMP6-mediated signaling and gene expression," J. Biol. Chem., 285(32):24783-24792.
Zhang, et al., (2010), "The role of hepatocyte hemojuvelin in the regulation of bone morphogenic protein-6 and hepcidin expression in vivo," J. Biol. Chem., 285(22):16416-16423.
Samad, et al., (2004), "DRAGON: A member of the Repulsive Guidance Molecule-Related Family of Neuronal- and Muscle-Expressed Membrane Proteins Is Regulated by DRG11 and Has Neuronal Adhesive Properties," J. Neurosci. 24:2027-2036.
Pinnix, et al., (2010), "Ferroportin and Iron Regulation in Breast Cancer Progression and Prognosis," Science Translational Medicine 2(43): 1-10.
Babitt et al. (2006) "Bone morphogenetic protein signaling by hemojuvelin regulates hepcidin expression," Nature Genetics. 38:531-539.
Babitt et al. (2007) "Modulation of bone morphogenetic protein signaling in vivo regulates systemic iron balance," J. Clin. Invest. 117:1933-1939.
European Search Report corresponding to European Patent Application No. 12779784.3, dated Aug. 21, 2014.

* cited by examiner

*Primary Examiner* — Michael Szperka
(74) *Attorney, Agent, or Firm* — Lathrop & Gage LLP

(57) ABSTRACT

The present disclosure relates to hemojuvelin-IgG Fc domain fusion proteins, variants, derivatives, fragments and peptide mimetics derived therefrom and methods of using these fusion proteins for the regulation of iron homeostasis and the treatment of diseases related to iron homeostasis.

39 Claims, 10 Drawing Sheets

COMPOSITIONS FOR REGULATING IRON HOMEOSTASIS AND METHODS OF USING SAME

RELATED APPLICATIONS

This application is a 35 U.S.C. §371 filing of International Application No. PCT/US2012/021829, filed Jan. 19, 2012; which claims priority to U.S. Provisional Patent Application No. 61/434,405 filed on Jan. 19, 2011. The entire contents of which are incorporated herein by reference.

RELATED APPLICATION

This application claims priority from U.S. Provisional Patent Application No. 61/434,405, filed on Jan. 19, 2011 and incorporated herein by reference in its entirety.

TECHNICAL FIELD

The present disclosure relates generally to therapy, prevention and amelioration of iron homeostasis disorders, particularly with respect to management of anemias. The present disclosure is more specifically related to hemojuvelin-immunoglobulin Fc domain fusion proteins and variants, derivatives and peptide mimetics derived therefrom and methods of using these compositions for altering serum iron, serum hemoglobin and/or hematocrit levels in humans.

BACKGROUND

Iron is an essential element required for growth and survival of almost every organism. Red blood cells (RBC) contain hemoglobin (Hb), a red, iron-rich protein that carries oxygen from the lungs to all of the body's muscles and organs where it reacts to provide the energy the body needs for its normal activities. When the number of red blood cells or the amount of hemoglobin they contain fall below normal, the body receives less oxygen and generates less energy than it needs to function properly. This condition in general is referred to as anemia. A common cause for anemia among infants and children is an iron deficiency. As many as 20% of children in the United States and 80% of children in developing countries will become anemic at some point by the age of 18 years. Martin, P. L., et al. The Anemias, Principles and Practices of Pediatrics, 1657 (2d ed., Lippincott 1994).

In mammals, the iron balance is primarily regulated at the level of duodenal absorption of dietary iron. In humans, hereditary hemochromatosis (HH) is a common autosomal recessive genetic disease caused by hyperabsorption of dietary iron leading to an iron overload in plasma and multiple organs, including in particular the pancreas, liver, and skin, and resulting in damages in these organs and tissues due to the iron deposits.

Juvenile hemochromatosis is an iron overload disorder caused by mutations in the gene encoding the major iron regulatory hormone hepcidin (HAMP) and hemojuvelin (HFE2). (Roetto, A., et al. 2003. *Nut. Genet.* 33:21-22; Papanikolaou, G., et al. 2004. *Nut. Genet.* 36:77-82.) It has been shown that hemojuvelin is a bone morphogenetic protein (BMP) co-receptor and that hemojuvelin-mediated BMP signals regulate hepcidin expression and iron metabolism. (Babitt, J. L., et al. 2006. *Nat. Genet.* 38:531-539; Babitt, J. L., et al. 2007. *J Clin Invest.* 117:1933-1939.) However, the endogenous BMP regulator(s) of hepcidin in vivo is unknown.

Hemojuvelin (also known as RGMc) is a member of the Repulsive Guidance Molecules family of proteins, including RGMa and DRAGON (RGMb), which share 50-60% amino acid identity. (Samad, T. A., et al. 2004. *J. Neurosci.* 24:2027-2036.).

There is a need for a cost-effective and efficient method for regulating hepcidin expression and iron metabolism.

SUMMARY

The present disclosure provides hemojuvelin ("HJV")-immunoglobulin Fc domain fusion proteins. The present disclosure also provides methods of using these proteins for the treatment of iron homeostasis disorders. The HJV may be mammalian HJV. More specifically, the HJV may be mouse or human HJV.

The present disclosure further provides a composition comprising a fusion protein or a variant, derivative or peptide mimetic derived therefrom 95% identical to the sequence of SEQ ID NO:9. In one embodiment, the fusion protein or a variant, derivative or peptide mimetic derived therefrom is at least 98% pure as determined by size exclusion chromatography. In another embodiment, the fusion protein or a variant, derivative or peptide mimetic derived therefrom is glycosylated. In certain embodiments, asparagine 83, asparagine 178 and asparagine 337 of SEQ ID NO. 1 and SEQ ID NO. 9 are N-glycoslyation sites. In one aspect of this embodiment, the glycosylation pattern is a mammalian glycosylation pattern. Specifically, the glycosylation pattern is from a Chinese hamster ovary (CHO) cell line.

In another embodiment, the N-terminal amino acid of the fusion protein or a variant, derivative or peptide mimetic derived therefrom is glutamine. In one aspect of this embodiment, the N-terminus of the fusion protein or a variant, derivative or peptide mimetic derived therefrom is QCKILRCNAE (SEQ ID NO:10). In another embodiment, the N-terminal fragment may be any fragment from the first 150 amino acids of SEQ ID NOs: 1 or 9.

In another embodiment, the composition is substantially pyrogen free. In another embodiment, the serum half-life of the fusion protein or a variant, derivative or peptide mimetic derived therefrom is at least 10 hours. In another embodiment, the fusion protein or a variant, derivative or peptide mimetic derived therefrom binds to bone morphogenic protein-6 ("BMP-6") with a $K_D$ of at least $10^{-7}$ M and inhibits BMP-6 signaling. In another embodiment, the composition increases hematocrit in a subject when administered. In another embodiment, the composition increases hematocrit to at least normal levels in an anemic subject when administered to the anemic subject for one month or more.

In another embodiment, the fusion protein or a variant, derivative or peptide mimetic derived therefrom forms a homodimer. In one aspect of this embodiment, the homodimer is formed in the Fc hinge region. More specifically, the homodimer is formed through a chemical interaction between cysteines 373, 380 and/or 383, in SEQ ID NO:9. Specifically, the chemical interaction is a disulfide bond.

The present disclosure also provides a nucleic acid molecule that encodes the fusion protein or a variant, derivative, fragment or peptide mimetic derived therefrom. In one embodiment, the nucleic acid molecule comprises a sequence 95% identical to the sequence of SEQ ID NO:11.

The present disclosure also provides a mammalian cell comprising the nucleic acid sequence that encodes the fusion protein or a variant, derivative, fragment or peptide mimetic derived therefrom. In one embodiment, the cell is a CHO cell.

The present disclosure also provides a method of treating an iron homeostasis disorder with resultant anemia in a subject in need thereof by administering a therapeutically effective amount of the composition described above to the subject, thereby treating the iron homeostasis disorder and improving anemia.

The present disclosure also provides a composition comprising a fusion protein or a variant, derivative, fragment or peptide mimetic derived therefrom wherein the fusion protein or a variant, derivative, fragment or peptide mimetic derived therefrom comprises an N-terminal polypeptide and a C-terminal polypeptide, wherein the N-terminal polypeptide comprises a sequence 95% identical to the sequence of SEQ ID NO: 1 and wherein the C-terminal peptide comprises a sequence 95% identical to a sequence selected from the group consisting of SEQ ID NOs: 3, 4, 5, 6, and 7. In one embodiment, the fusion protein or a variant, derivative, fragment or peptide mimetic derived therefrom is at least 98% pure as determined by size exclusion chromatography.

In another embodiment, the fusion protein or a variant, derivative, fragment or peptide mimetic derived therefrom is glycosylated. In one aspect of this embodiment, the glycosylation pattern is a mammalian glycosylation pattern. Specifically, the glycosylation pattern is from a Chinese hamster ovary (CHO) cell line.

In another embodiment, the N-terminal amino acid of the fusion protein or a variant, derivative, fragment or peptide mimetic derived therefrom is glutamine. In one aspect of this embodiment, the N-terminus of the fusion protein or a variant, derivative, fragment or peptide mimetic derived therefrom is QCKILRCNAE (SEQ ID NO:10).

In another embodiment, the composition is substantially pyrogen free. In another embodiment, the serum half-life of the fusion protein or a variant, derivative or peptide mimetic derived therefrom is at least 10 hours. In another embodiment, the fusion protein or a variant, derivative or peptide mimetic derived therefrom binds to bone morphogenic protein-6 ("BMP-6") with a $K_D$ of at least $10^{-7}$ M and inhibits BMP-6 signaling. In another embodiment, the composition increases hematocrit in a subject when administered. In another embodiment, the composition increases hematocrit to at least normal levels in an anemic subject when administered to the anemic subject for one month or more.

The present disclosure also provides a nucleic acid molecule that encodes the fusion protein or a variant, derivative, fragment or peptide mimetic derived therefrom. In one embodiment, the nucleic acid sequence comprises SEQ ID NO:11.

The present disclosure also provides a mammalian cell comprising the nucleic acid sequence that encodes the fusion protein or a variant, derivative, fragment or peptide mimetic derived therefrom. In one embodiment, the cell is a CHO cell.

The present disclosure also provides a method of treating an iron homeostasis disorder and/or improving anemia in a subject in need thereof by administering a therapeutically effective amount of the composition described above to the subject, thereby treating the iron homeostasis disorder and/or improving anemia.

The present disclosure also provides a method of treating a cancer in a subject in need thereof by administering a therapeutically effective amount of the composition described above to the subject, thereby treating the cancer.

BRIEF DESCRIPTION OF THE FIGURES

Figure 1:
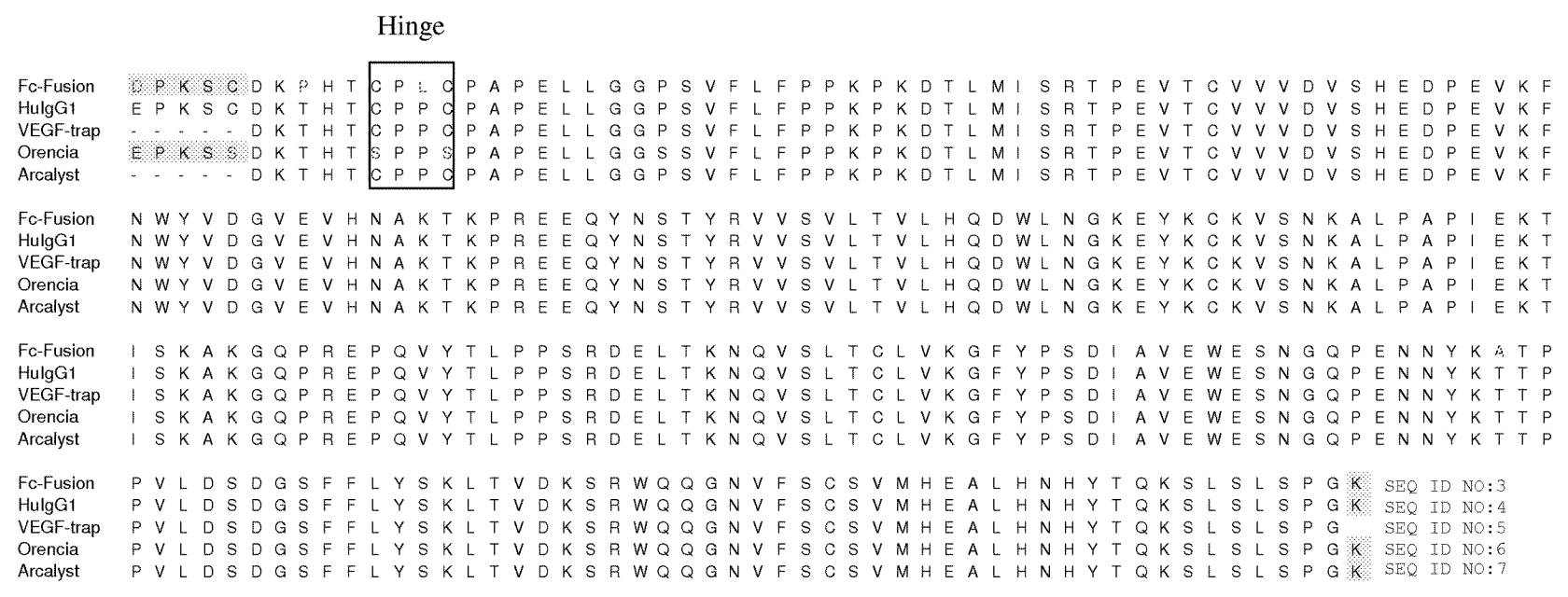

FIG. 1 shows an alignment of the amino acid sequences of SEQ ID NOs 3-7.

DETAILED DESCRIPTION

Figure 2:
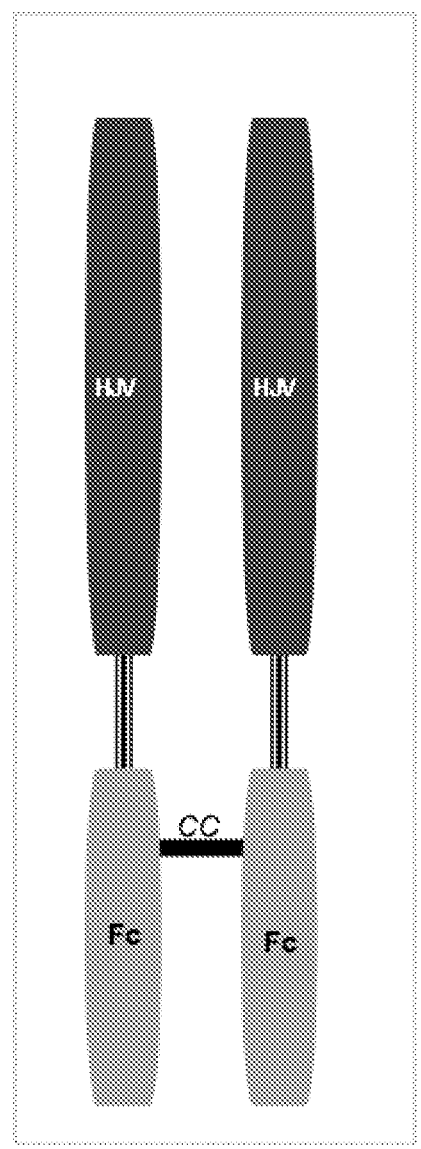
FIG. 2 shows a schematic of an HJV.Fc dimer.

The inventors have found new therapeutic compositions for the treatment of anemia. These compositions are fusion proteins comprising hemojuvelin ("HJV") and an IgG Fc region and variants, derivatives, fragments and peptide mimetics derived therefrom. The present disclosure provides fusion proteins comprising a peptide comprising at least a portion of the amino acid sequence of HJV fused to an IgG Fc region or a derivative thereof. In certain embodiments, the HJV portion of the fusion protein is the N-terminal portion of the fusion protein and the IgG Fc portion of the fusion protein is the C-terminal portion. In other embodiments, the HJV portion of the fusion protein is the C-terminal portion of the fusion protein and the IgG Fc portion of the fusion protein is the N-terminal portion.

In certain embodiments, the N-terminal and C-terminal portions of the fusion protein are joined with a linker. In specific embodiments, the linker is a polypeptide between 1 and 50 amino acids in length. In more specific embodiments, the linker is between 2 and 25 amino acids in length. In more specific embodiments, the linker is between 3 and 15 amino acids in length. In more specific embodiments, the linker is 4, 5, 6, 7, 8 or 9 amino acids in length. In one preferred embodiment, the linker is 5 amino acids in length. In certain embodiments, a linker may be rich in glycine and proline residues and my, for example, contain a single sequence of threonine/serine and glycines or repeating sequences of threonine/serine and glycine (e.g. TG). In certain embodiments, mutations may be made in the linker (if any) and or the Fc protein to alter the half-life of the protein.

Administration of the fusion proteins of the present disclosure or variants, derivatives, fragments and peptide mimetics derived therefrom results in decreased hepcidin expression. The compositions described herein can be used to treat iron metabolism disorders and to increase serum hemoglobin and hematocrit.

The HJV Portion

The human hemojuvelin ("HJV") portion of the fusion protein described herein comprises a soluble portion of HJV that is able to increase mobilization of iron and/or treat or ameliorate at least one symptom associated with an iron metabolism disease. In some embodiments, the HJV portion of the fusion protein of the present disclosure is at least 75% (e.g., at least 80%, at least 85%, at least 90%, at least 95%, at least 96%, at least 97%, at least 98%, or at least 99%) identical to a portion of SEQ ID NO:1.

The amino acid sequence of HJV is shown in Table 1 below:

TABLE 1

Amino acid sequence of human HJV without the N-terminal signal
sequence or C-terminal GPI domain (364 amino acids; SEQ ID NO: 1)

```
          10         20         30         40         50         60
     QCKILRCNAE YVSSTLSLRG GGSSGALRGG GGGGRGGGVG SGGLCRALRS YALCTRRTAR 70         80         90        100        110        120
     TCRGDLAFHS AVHGIEDLMI QHNCSRQGPT APPPPRGPAL PGAGSGLPAP DPCDYEGRFS 130        140        150        160        170        180
     RLHGRPPGFL HCASFGDPHV RSFHHHFHTC RVQGAWPLLD NDFLFVQATS SPMALGANAT 190        200        210        220        230        240
     ATRKLTIIFK NMQECIDQKV YQAEVDNLPV AFEDGSINGG DRPGGSSLSI QTANPGNHVE 250        260        270        280        290        300
     IQAAYIGTTI IIRQTAGQLS FSIKVAEDVA MAFSAEQDLQ LCVGGCPPSQ RLSRSERNRR 310        320        330        340        350        360
     GAITIDTARR LCKEGLPVED AYFHSCVFDV LISGDPNFTV AAQAALEDAR AFLPDLEKLH
         364
     LFPS
```

In certain embodiments, the HJV portion of the fusion protein described herein is any fragment of SEQ ID NO:1 that is soluble in aqueous solution and is able to mobilize iron and/or treat or ameliorate at least one symptom associated with an iron metabolism disease. Fragments of SEQ ID NO:1 that make up the HJV portion of the fusion protein of the present disclosure include fragments of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350 or 360 amino acids of SEQ ID NO:1. These fragments can comprise any range of amino acids of SEQ ID NO:1. In some specific embodiments, fragments comprise 10, 20, 30, 40, 50, 60, 70, 80, 90, 100, 110, 120, 130, 140 or 150 amino acids of amino acids 1-150 of SEQ ID NO:1. In certain embodiments, the HJV portion of the fusion protein of the present disclosure has greater than 80, 85, 90, 95, 97, 98, or 99% identity to the fragments of SEQ ID NO:1, wherein the fragments include 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350 or 360 amino acids of SEQ ID NO:1.

Fragments of SEQ ID NO:1 that make up the HJV portion of the fusion protein of the present disclosure include fragments of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350 or 360 consecutive amino acids of SEQ ID NO:1. In certain embodiments, the HJV portion of the fusion protein of the present disclosure has greater than 80, 85, 90, 95, 97, 98, or 99% identity to the fragments of SEQ ID NO:1, wherein the fragments include 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350 or 360 consecutive amino acids of SEQ ID NO:1.

In certain embodiments, the HJV portion of the fusion protein of the present disclosure is full length or a fragment and has greater than 75% identity to SEQ ID NO:1. In other embodiments, the HJV portion of the fusion protein of the present disclosure is full length or a fragment and has greater than 80, 85, 90, 95, 97, 98, or 99% identity to SEQ ID NO:1. In certain specific embodiments, the differences between SEQ ID NO:1 and the HJV portion of the fusion protein of the present disclosure are conservative amino acid changes, as described below.

The IgG Fc Portion

The IgG Fc portion of the fusion protein of the present disclosure comprises at least a portion of the Fc region of an immunoglobulin or a derivative thereof which, when fused with the HJV portion of the fusion protein of the present disclosure, is able to mobilize iron and/or treat or ameliorate at least one symptom associated with an iron metabolism disease. The IgG Fc portion of the fusion protein of the present disclosure stabilized the fusion protein when administered to a subject. In specific embodiments, the attachment of an IgG Fc or variant, derivative, fragment or peptide mimetic derived therefrom makes the serum half-life of the serum protein greater than 1, 2, 3, 4, 5, 6, 7, 8, 9, 10, 11, 12, 13, 14, 15, 15, 17, 18, 19, 20, 21, 22, 23, 24, 36, 48, 60, 72, 84, or 96 hours. There are several sequences compatible with the fusion protein of the present disclosure.

In certain embodiments, the IgG Fc domain includes CH2 and CH3 domains and a hinge region. In other embodiments, the IgG Fc also contains at least a portion of the CH1 region. In specific embodiments, the HJV portion of the fusion protein is directly linked to the hinge region. In other embodiments, the Fc domain contains sequence N-terminal to the hinge region from its CH1 domain which is linked to the HJV portion of the fusion protein. In other embodiments, a linker is attached to the hinge region, or the CH1 domain on the Fc domain. In more specific embodiments, the hinge region comprises 4 amino acids with the consensus sequence $X_1$-P-$X_2$-$X_3$ (SEQ ID NO:2), wherein $X_1$ is cysteine or serine, $X_2$ is leucine or proline, and $X_3$ is cysteine or serine. The hinge region of an intact immunoglobulin provides the protein sufficient flexibility for effective antigen-antibody binding. In certain embodiments of the present disclosure, the hinge region is included in the IgG Fc portion of the fusion protein of the present disclosure to maintain its flexibility, especially when the fusion protein is in the dimer form.

In certain embodiments, the IgG Fc portion of the fusion protein of the present disclosure is at least 75% (e.g., at least 80%, at least 85%, at least 90%, at least 95%, at least 96%, at least 97%, at least 98%, or at least 99%) identical to a portion of SEQ ID NO:3.

Other sequences or fragments of derivatives thereof are compatible for use as the IgG Fc portion of the fusion protein of the present disclosure. An alignment of the IgG Fc derivative (SEQ ID NO:3), human IgG1 Fc (SEQ ID NO:4), the Fc region from the VEGFR-Fc fusion developed by Regeneron (SEQ ID NO:5), the Fc region from the CTLA4-Fc fusion (ORENCIA™ or abatacept) developed by Bristol Myers Squibb (SEQ ID NO:6), the Fc region from the IL 1R-Fc fusion (ARCALYST™ or rilonacept) developed by Regeneron (SEQ ID NO:7) and the Fc region from HUMIRA® (adaluminab).

In certain embodiments, the IgG Fc portion of the fusion protein of the present disclosure is any fragment of SEQ ID

TABLE 2

Amino acid sequence of an IgG Fc region derivative
(232 amino acids; SKI ID NO: 3)

```
        10          20          30          40          50          60
DPKSCDKPHT  CPLCPAPELL  GGPSVFLFPP  KPKDTLMISR  TPEVTCVVVD  VSHEDPEVKF 70          80          90         100         110         120
NWYVDGVEVH  NAKTKPREEQ  YNSTYRVVSV  LTVLHQDWLN  GKEYKCKVSN  KALPAPIEKT 130         140         150         160         170         180
ISKAKGQPRE  PQVYTLPPSR  DELTKNQVSL  TCLVKGFYPS  DIAVEWESNG  QPENNYKATP 190         200         210         220        230   232
PVLDSDGSFF  LYSKLTVDKS  RWQQGNVFSC  SVMHEALHNH  YTQKSLSLSP  GK
```

In certain embodiments, the IgG Fc portion of the fusion protein of the present disclosure is any fragment of SEQ ID NO:3 which, when fused with the HJV portion of the fusion protein of the present disclosure, is soluble in aqueous solution and is able to mobilize iron and/or treat or ameliorate at least one symptom associated with an iron metabolism disease. Fragments of SEQ ID NO:3 that make up the IgG Fc portion of the fusion protein of the present disclosure include fragments of 10, 20, 30, 40, 50, 60, 70, 80, 90, 100, 110, 120, 130, 140, 150, 160, 170, 180, 190, 200, 210, 220 or 230 amino acids of SEQ ID NO:3. In certain embodiments, the IgG Fc portion of the fusion protein of the present disclosure has greater than 80, 85, 90, 95, 97, 98, or 99% identity to the fragments of SEQ ID NO: 3, wherein the fragments include 10, 20, 30, 40, 50, 60, 70, 80, 90, 100, 110, 120, 130, 140, 150, 160, 170, 180, 190, 200, 210, 220, or 230 amino acids of SEQ ID NO: 3.

Fragments of SEQ ID NO:3 that make up the IgG Fc portion of the fusion protein of the present disclosure include fragments of 10, 20, 30, 40, 50, 60, 70, 80, 90, 100, 110, 120, 130, 140, 150, 160, 170, 180, 190, 200, 210, 220 or 230 consecutive amino acids of SEQ ID NO:3. In certain embodiments, the IgG Fc portion of the fusion protein of the present disclosure has greater than 80, 85, 90, 95, 97, 98, or 99% identity to the fragments of SEQ ID NO:3, wherein the fragments include 10, 20, 30, 40, 50, 60, 70, 80, 90, 100, 110, 120, 130, 140, 150, 160, 170, 180, 190, 200, 210, 220, or 230 consecutive amino acids of SEQ ID NO: 3.

In certain embodiments, the IgG Fc portion of the fusion protein of the present disclosure is full length or a fragment and has greater than 75% identity to SEQ ID NO:3. In other embodiments, the IgG Fc portion of the fusion protein of the present disclosure is full length or a fragment and has greater than 80, 85, 90, 95, 97, 98, or 99% identity to SEQ ID NO:3. In certain specific embodiments, the differences between SEQ ID NO:3 and the IgG Fc portion of the fusion protein of the present disclosure are conservative amino acid changes, as described below.

NOs:4, 5, 6 or 7 which, when fused with the HJV portion of the fusion protein of the present disclosure, is soluble in aqueous solution and is able to mobilize iron and/or treat or ameliorate at least one symptom associated with an iron metabolism disease. Fragments of SEQ ID NOs:4, 5, 6 or 7 that make up the IgG Fc portion of the fusion protein of the present disclosure include fragments of 10, 20, 30, 40, 50, 60, 70, 80, 90, 100, 110, 120, 130, 140, 150, 160, 170, 180, 190, 200, 210, 220 or 230 amino acids of SEQ ID NOs:4, 5, 6 or 7. In certain embodiments, the IgG Fc portion of the fusion protein of the present disclosure has greater than 80, 85, 90, 95, 97, 98, or 99% identity to the fragments of SEQ ID NO:3, wherein the fragments include 10, 20, 30, 40, 50, 60, 70, 80, 90, 100, 110, 120, 130, 140, 150, 160, 170, 180, 190, 200, 210, 220, or 230 amino acids of SEQ ID NOs:4, 5, 6 or 7.

Fragments of SEQ ID NOs:4, 5, 6 or 7 that make up the IgG Fc portion of the fusion protein of the present disclosure include fragments of 10, 20, 30, 40, 50, 60, 70, 80, 90, 100, 110, 120, 130, 140, 150, 160, 170, 180, 190, 200, 210, 220 or 230 consecutive amino acids of SEQ ID NOs:4, 5, 6 or 7. In certain embodiments, the IgG Fc portion of the fusion protein of the present disclosure has greater than 80, 85, 90, 95, 97, 98, or 99% identity to the fragments of SEQ ID NO:3, wherein the fragments include 10, 20, 30, 40, 50, 60, 70, 80, 90, 100, 110, 120, 130, 140, 150, 160, 170, 180, 190, 200, 210, 220, or 230 consecutive amino acids of SEQ ID NOs:4, 5, 6 or 7.

In certain embodiments, the IgG Fc portion of the fusion protein of the present disclosure is full length or a fragment and has greater than 75% identity to SEQ ID NOs:4, 5, 6 or 7. In other embodiments, the IgG Fc portion of the fusion protein of the present disclosure is full length or a fragment and has greater than 80, 85, 90, 95, 97, 98, or 99% identity to SEQ ID NOs:4, 5, 6 or 7. In certain specific embodiments, the differences between SEQ ID NOs:4, 5, 6 or 7 and the IgG Fc portion of the fusion protein of the present disclosure are conservative amino acid changes, as described below.

The Linker

In certain embodiments, the fusion protein of the present disclosure includes a linker connecting the HJV portion and the IgG Fc portion of the fusion protein. In preferred embodiments, the linker is a peptide. In alternative embodiments, the peptide can be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 amino acids in length. In certain embodiments, the amino acids making up the linker are glycine or serine at each position. In one preferred embodiment, the linker has the sequence GGGGG (SEQ ID NO:8).

In certain embodiments, a linker may be rich in glycine and proline residues and my, for example, contain a single sequence of threonine/serine and glycines or repeating sequences of threonine/serine and glycine (e.g. TG).

In certain embodiments, mutations may be made in the linker (if any) and or the Fc protein to alter the half-life of the protein.

Dimerization

In certain embodiments, the fusion protein is in the form of a dimer including two identical polypeptide subunits. In the embodiment shown schematically in FIG. 2, each polypeptide subunit, from the N-terminal to C-terminal, includes the polypeptide sequence of SEQ ID NO:9, shown below.

TABLE 3

Amino acid sequence of an HJV.Fc fusion protein of the invention (596 amino acids; SEQ ID NO: 9)

```
         10         20         30         40         50         60
 QCKILRCNAE YVSSTLSLRG GGSSGALRGG GGGGRGGGVG SGGLCRALRS    YALCTRRTAR 70         80         90        100        110        120
 TCRGDLAFHS AVHGIEDLMI QHNCSRQGPT APPPPRGPAL PGAGSGLPAP    DPCDYEGRFS 130        140        150        160        170        180
 RLHGRPPGFL HCASFGDPHV RSFHHHFHTC RVQGAWPLLD NDFLFVQATS    SPMALGANAT 190        200        210        220        230        240
 ATRKLTIIFK NMQECIDQKV YQAEVDNLPV AFEDGSINGG DRPGGSSLSI    QTANPGNHVE 250        260        270        280        290        300
 IQAAYIGTTI IIRQTAGQLS FSIKVAEDVA MAFSAEQDLQ LCVGGCPPSQ    RLSRSERNRR 310        320        330        340        350        360
 GAITIDTARR LCKEGLPVED AYFHSCVFDV LISGDPNFTV AAQAALEDAR    AFLPDLEKLH 370        380        390        400        410        420
 LFPSDPKSCD KPHTCPLCPA PELLGGPSVF LFPPKPKDTL MISRTPEVTC    VVVDVSHEDP 430        440        450        460        470        480
 EVKFNWYVDG VEVHNAKTKP REEQYNSTYR VVSVLTVLHQ DWLNGKEYKC    KVSNKALPAP 490        500        510        520        530        540
 IEKTISKAKG QPREPQVYTL PPSRDELTKN QVSLTCLVKG FYPSDIAVEW    ESNGQPENNY 550        560        570        580        590        594
 KATPPVLDSD GSFFLYSKLT VDKSRWQQGN VFSCSVMHEA LHNHYTQKSL    SLSPGK
```

The two polypeptide subunits are connected together by disulfide bonds between the respective hinge regions to form the dimer structure. The homodimer can be formed in the Fc hinge region. More specifically, the homodimer can be formed through a chemical interaction between cysteines 373, 380 and/or 383, in SEQ ID NO:9.

The nucleic acid sequence of the vector used to express a protein with an amino acid sequence of SEQ ID NO:9 is shown below.

TABLE 4

Nucleic acid sequence of vector that encodes SEQ ID NO: 9.
(SEQ ID NO: 11)

```
ttctagagaa tccagacatg ataagataca ttgatgagtt tggacaaacc acaactagaa    60
tgcagtgaaa aaaatgcttt atttgtgaaa tttgtgatgc tattgcttta tttgtaacca   120
ttataagctg caataaacaa gttaacaaca acaattgcat tcattttatg tttcaggttc   180 aggggggaggt gtgggaggtt ttttaaagca agtaaaacct ctacaaatgt ggtatggctg   240
attatgatca atcgatgtcg accaattcgt aatcatgtca tagctgtttc ctgtgtgaaa   300
ttgttatccg ctcacaattc cacacaacat acgagccgga agcataaagt gtaaagcctg   360
gggtgcctaa tgagtgagct aactcacatt aattgcgttg cgctcactgc ccgctttcca   420
```

TABLE 4-continued

```
gtcgggaaac ctgtcgtgcc agctgcatta atgaatcggc caacgcgcgg ggagaggcgg    480
tttgcgtatt gggcgctctt ccgcttcctc gctcactgac tcgctgcgct cggtcgttcg    540
gctgcggcga gcggtatcag ctcactcaaa ggcggtaata cggttatcca cagaatcagg    600
ggataacgca ggaaagaaca tgtgagcaaa aggccagcaa aaggccagga accgtaaaaa    660
ggccgcgttg ctggcgtttt tccataggct ccgcccccct gacgagcatc acaaaaatcg    720
acgctcaagt cagaggtggc gaaacccgac aggactataa agataccagg cgtttccccc    780
tggaagctcc ctcgtgcgct ctcctgttcc gaccctgccg cttaccggat acctgtccgc    840
ctttctccct tcgggaagcg tggcgctttc tcatagctca cgctgtaggt atctcagttc    900
ggtgtaggtc gttcgctcca gctgggctg tgagcacgaa cccccgttc agcccgaccg     960
ctgcgcctta tccggtaact atcgtcttga gtccaacccg gtaagacacg acttatcgcc   1020
actggcagca gccactggta acaggattag cagagcgagg tatgtaggcg gtgctacaga   1080
gttcttgaag tggtggccta actacggcta cactagaaga acagtatttg gtatctgcgc   1140
tctgctgaag ccagttacct tcggaaaaag agttggtagc tcttgatccg gcaaacaaac   1200
caccgctggt agcggtggtt tttttgtttg caagcagcag attacgcgca gaaaaaaagg   1260
atctcaagaa gatcctttga tcttttctac ggggtctgac gctcagtgga acgaaaactc   1320
acgttaaggg attttggtca tgagattatc aaaaaggatc ttcacctaga tccttttaaa   1380
ttaaaaatga agttttaaat caatctaaag tatatatgag taaacttggt ctgacagtta   1440
ccaatgctta atcagtgagg cacctatctc agcgatctgt ctatttcgtt catccatagt   1500
tgcctgactc cccgtcgtgt agataactac gatacgggag ggcttaccat ctggccccag   1560
tgctgcaatg ataccgcgag acccacgctc accggctcca gatttatcag caataaacca   1620
gccagccgga agggccgagc gcagaagtgg tcctgcaact ttatccgcct ccatccagtc   1680
tattaattgt tgccgggaag ctagagtaag tagttcgcca gttaatagtt tgcgcaacgt   1740
tgttgccatt gctacaggca tcgtggtgtc acgctcgtcg tttggtatgg cttcattcag   1800
ctccggttcc caacgatcaa ggcgagttac atgatccccc atgttgtgca aaaaagcggt   1860
tagctccttc ggtcctccga tcgttgtcag aagtaagttg gccgcagtgt tatcactcat   1920
ggttatggca gcactgcata attctcttac tgtcatgcca tccgtaagat gcttttctgt   1980
gactggtgag tactcaacca agtcattctg agaatagtgt atgcggcgac cgagttgctc   2040
ttgcccggcg tcaatacggg ataataccgc gccacatagc agaactttaa aagtgctcat   2100
cattggaaaa cgttcttcgg ggcgaaaact ctcaaggatc ttaccgctgt tgagatccag   2160
ttcgatgtaa cccactcgcg cacccaactg atcttcagca tcttttactt tcaccagcgt   2220
ttctgggtga gcaaaaacag gaaggcaaaa tgccgcaaaa aagggaataa gggcgacacg   2280
gaaatgttga atactcatac tcttcctttt tcaatattat tgaagcattt atcagggtta   2340
ttgtctcatg agcggataca tatttgaatg tatttagaaa aataaacaaa taggggttcc   2400
gcgcacattt ccccgaaaag tgccacctga cgtctaagaa accattatta tcatgacatt   2460
aacctataaa aataggcgta tcacgaggcc ctttcgtctc gcgcgtttcg gtgatgacgg   2520
tgaaaacctc tgacacatgc agctcccgga cggtcaca gcttgtctgt aagcggatgc     2580
cgggagcaga caagcccgtc agggcgcgtc agcgggtgtt ggcgggtgtc ggggctggct   2640
taactatgcg gcatcagagc agattgtact gagagcgcac catatgcggt gtgaaatacc   2700
gcacagatgc gtaaggagaa aataccgcat caggcgccat tcgccattca ggctgcgcaa   2760
ctgttgggaa gggcgatcgg tgcgggcctc ttcgctatta cgccagctgg cgaaaggggg   2820
```

TABLE 4-continued

```
atgtgctgca aggcgattaa gttgggtaac gccagggttt tcccagtcac gacgttgtaa   2880
aacgacggcc agtgccaagc tagcggccgc cacgagtcta gctagagtac gaattcgagc   2940
tcggaacccc tatacattga atcaatattg gcaattagcc atattagtca ttggttatat   3000
agcataaatc aatattggct attggccatt gcatacgttg tatctatatc ataatatgta   3060
catttatatt ggctcatgtc caatatgacc gccatgttga cattgattat tgactagtta   3120
ttaatagtaa tcaattacgg ggtcattagt tcatagccca tatatggagt tccgcgttac   3180
ataacttacg gtaaatggcc cgcctggctg accgcccaac gacccccgcc cattgacgtc   3240
aataatgacg tatgttccca tagtaacgcc aatagggact ttccattgac gtcaatgggt   3300
ggagtattta cggtaaactg cccacttggc agtacatcaa gtgtatcata tgccaagtcc   3360 gcccctatt gacgtcaatg acggtaaatg gcccgcctgg cattatgccc agtacatgac   3420
cttacgggac tttcctactt ggcagtacat ctacgtatta gtcatcgcta ttaccatggt   3480
gatgcggttt tggcagtaca ccaatgggcg tggatagcgg tttgactcac ggggatttcc   3540
aagtctccac cccattgacg tcaatgggag tttgttttgg caccaaaatc aacgggactt   3600
tccaaaatgt cgtaataacc ccgccccgtt gacgcaaatg ggcggtaggc gtgtacggtg   3660
ggaggtctat ataagcagag ctcgtttagt gaaccgtcag atcggggatc cgatatccac   3720
catgggggag ccaggccagt cccctagtcc caggtcctcc catggcagtc ccccaactct   3780
aagcactctc actctcctgc tgctcctctg tggacatgct cattctcaat gcaagatcct   3840
ccgctgcaat gctgagtacg tatcgtccac tctgagcctt agaggtgggg gttcatcagg   3900
agcacttcga ggaggaggag gaggaggccg gggtggaggg gtgggctctg gcggcctctg   3960
tcgagccctc cgctcctatg cgctctgcac tcggcgcacc gcccgcacct gccgcgggga   4020
cctcgccttc cattcggcgg tacatggcat cgaagacctg atgatccagc acaactgctc   4080
ccgccagggc cctacagccc ctcccccgcc ccggggcccc gcccttccag gcgcgggctc   4140
cggcctccct gccccggacc cttgtgacta tgaaggccgg ttttcccggc tgcatggtcg   4200
tcccccgggg ttcttgcatt gcgcttcctt cggggacccc catgtgcgca gcttccacca   4260
tcactttcac acatgccgtg tccaaggagc ttggcctcta ctggataatg acttcctctt   4320
tgtccaagcc accagctccc ccatggcgtt gggggccaac gctaccgcca cccggaagct   4380
caccatcata tttaagaaca tgcaggaatg cattgatcag aaggtgtatc aggctgaggt   4440
ggataatctt cctgtagcct ttgaagatgg ttctatcaat ggaggtgacc gacctggggg   4500
atccagtttg tcgattcaaa ctgctaaccc tgggaaccat gtggagatcc aagctgccta   4560
cattggcaca actataatca ttcggcagac agctgggcag ctctccttct ccatcaaggt   4620
agcagaggat gtggccatgg ccttctcagc tgaacaggac ctgcagctct gtgttggggg   4680
gtgccctcca agtcagcgac tctctcgatc agagcgcaat cgtcggggag ctataaccat   4740
tgatactgcc agacggctgt gcaaggaagg cttccagtg gaagatgctt acttccattc   4800
ctgtgtcttt gatgttttaa tttctggtga tcccaacttt accgtggcag ctcaggcagc   4860
actggaggat gcccgagcct tcctgccaga cttagagaag ctgcatctct tccctcagg   4920 tggtggtggt ggtgatccca aatcttgtga caaacctcac acatgcccac tgtgcccagc   4980
acctgaactc ctgggggac cgtcagtctt cctcttcccc ccaaaaccca aggacaccct   5040
catgatctcc cggacccctg aggtcacatg cgtggtggtg gacgtgagcc acgaagaccc   5100
tgaggtcaag ttcaactggt acgtggacgg cgtggaggtg cataatgcca agacaaagcc   5160
gcgggaggag cagtacaaca gcacgtaccg tgtggtcagc gtcctcaccg tcctgcacca   5220
```

TABLE 4-continued

```
ggactggctg aatggcaagg agtacaagtg caaggtctcc aacaaagccc tcccagcccc 5280
catcgagaaa accatctcca aagccaaagg gcagccccga gaaccacagg tgtacaccct 5340
gcccccatcc cgggatgagc tgaccaagaa ccaggtcagc ctgacctgcc tagtcaaagg 5400
cttctatccc agcgacatcg ccgtggagtg ggagagcaat gggcagccgg agaacaacta 5460
caaggccacg cctcccgtgc tggactccga cggctccttc ttcctctaca gcaagctcac 5520
cgtggacaag agcaggtggc agcagggaa cgtcttctca tgctccgtga tgcatgaggc 5580
tctgcacaac cactacacgc agaagagcct ctccctgtct ccgggtaaat gagctgat   5638
```

Nucleic acids 14-250 of SEQ ID NO:11 form an SV40 polyadenosine. Nucleic acids 643-1297 form the origin of replication. Nucleic acids 1438-2413 encode β-lacatamase. Nucleic acids 2932-3706 form a CMV promoter. Nucleic acids 3722-3826 encode the HJV leader. Nucleic acids 3827-4918 encode human HJV. Nucleic acids 4919-4933 encode a glycine spacer. Nucleic acids 4934-5629 encode an IgG Fc. SEQ ID NO:11 is shown schematically in Figures According to certain embodiments, the fusion protein of the present disclosure must form a dimer. In certain embodiments, the fusion protein forms a dimer but does not form higher order aggregates such as 4 mers, 6mers, 8mers, etc. These higher order associations can affect the solubility of the fusion protein and its therapeutic effectiveness.

Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of compositions and methods described herein will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present disclosure:

A "mammal" for purposes of treating infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present disclosure, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of a composition effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The terms "nucleic acid" and "polynucleotide" are used interchangeably herein to refer to single- or double-stranded RNA, DNA, PNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this disclosure are amino acid subsequences comprising CDRs and being capable of binding an antigen or Influenza A-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the present disclosure and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the present disclosure and evaluating one or more biological activities of the polypeptide as described herein and/or using any of a number of techniques well known in the art.

Modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant or portion of a polypeptide of the present disclosure, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As outlined above, amino acid substitutions are generally therefore based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the present disclosure. Software for performing BLAST analyses is publicly available through the National Center for Biotechnology Information.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the present disclosure, in bacterial or eukaryotic cells. Suitable vectors are disclosed below.

The term "variant" refers to a protein or polypeptide in which one or more amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). Preferred variants include alanine substitutions at one or more of amino acid positions. Other preferred substitutions include conservative substitutions that have little or no effect on the overall net charge, polarity, or hydrophobicity of the protein. Conservative substitutions are set forth above.

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. The term "variant" also encompasses polypeptides that have the amino acid sequence of the proteins/ peptides of the present disclosure with at least one and up to 25 (e.g., 1, 2, 3, 4, 5, 6, 7, 8, 9, 10, 15, 20) additional amino acids flanking either the 3' or 5' end of the amino acid sequence or both.

The term "variant" also refers to a protein that is at least 60 to 99 percent identical (e.g., 60, 65, 70, 75, 80, 85, 90, 95, 98, 99, or 100%, inclusive) in its amino acid sequence of the proteins of the present disclosure as determined by standard methods that are commonly used to compare the similarity in position of the amino acids of two polypeptides. The degree of similarity or identity between two proteins can be readily calculated by known methods. Preferred methods to determine identity are designed to give the largest match between the sequences tested. Methods to determine identity and similarity are codified in publicly available computer programs. Variants will typically have one or more (e.g., 2, 3, 4, 5, etc.) amino acid substitutions, deletions, and/or insertions as compared with the comparison protein or peptide, as the case may be.

A "mature" form of a fusion protein disclosed in the present disclosure is the product of a naturally occurring polypeptide or precursor form or proprotein. The naturally occurring polypeptide, precursor or proprotein includes, by way of nonlimiting example, the full length gene product encoded by the corresponding gene. Alternatively, it may be defined as the polypeptide, precursor or proprotein encoded by an open reading frame described herein. The product "mature" form arises, by way of nonlimiting example, as a result of one or more naturally occurring processing steps that may take place within the cell (e.g., host cell) in which the gene product arises. Examples of such processing steps leading to a "mature" form of a polypeptide or protein include the cleavage of the N terminal methionine residue encoded by the initiation codon of an ORF, or the proteolytic cleavage of a signal peptide or leader sequence. Further as used herein, a "mature" form of a polypeptide or protein may arise from a step of post translational modification other than a proteolytic cleavage event. Such additional processes include, by way of non limiting example, glycosylation, myristylation or phosphorylation. In general, a mature polypeptide or protein may result from the operation of only one of these processes, or a combination of any of them.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination.

The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well. Examples of such derivatives include (i) N-acyl derivatives of the amino terminal or of another free amino group, wherein the acyl group may be an alkanoyl group (e.g., acetyl, hexanoyl, octanoyl), an aroyl group (e.g., benzoyl) or a blocking group such as F-moc (fluorenylmethyl-O—CO—); (ii) esters of the carboxy terminal or of another free carboxy or hydroxyl group; (iii) amide of the carboxy terminus or of another free carboxyl group produced by reaction with ammonia or with a suitable amine; (iv) phosphorylated derivatives; (v) derivatives conjugated to an antibody or other biological ligand and other types of derivatives.

The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well. A cyclic derivative containing an intramolecular disulfide bond may be prepared by conventional solid phase synthesis while incorporating suitable S-protected cysteine or homocysteine residues at the positions selected for cyclization such as the amino and carboxy termini Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure; or (2) by removal of the peptide from the support along with complete side chain deprotection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S— alkyl bonds can be prepared by conventional solid phases while incorporating an amino acid residue with a suitable amino-protected side chain, and a suitable S-protected cysteine or homocysteine residue at the position selected for cyclization.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present disclosure may be all L, all D or mixed D, L peptide. In a preferred embodiment, the peptides consist of all D-amino acids. The presence of an N-terminal or C-terminal D-amino acid increases the in vivo stability of a peptide since peptidases cannot utilize a D-amino acid as a substrate.

Substitution of unnatural amino acids for natural amino acids in a subsequence of the peptides can also confer resistance to proteolysis. Such a substitution can, for instance, confer resistance to proteolysis by exopeptidases acting on the N-terminus. Such substitutions have been described and these substitutions do not affect biological activity. Examples of non-naturally occurring amino acids include α,α-disubstituted amino acids, N-alkyl amino acids, lactic acids, C-α-methyl amino acids, and β-methyl amino acids Amino acid analogs useful in the present disclosure may include but are not limited to β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formyl-methionine, 3-methylhistidine and other unconventional amino acids. Furthermore, the synthesis of peptides with unnatural amino acids is routine and known in the art.

One other effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini Certain chemical modifications, in particular N-terminal glycosylation, have been shown to increase the stability of peptides in human serum. Other chemical modifications which enhance serum stability include, but are not limited to, the addition of an N-terminal alkyl group, consisting of a lower alkyl of from 1 to 20 carbons, such as an acetyl group, and/or the addition of a C-terminal amide or substituted amide group. In particular the present disclosure includes modified peptides consisting of peptides bearing an N-terminal acetyl group and/or a C-terminal amide group.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

Peptide mimetics include reverse-D peptides which contain D-amino acids arranged in a reverse sequence relative to a peptide containing L-amino acids. For example, the C-terminal residue of an L-amino acid peptide becomes N-terminal for the D-amino acid peptide, and so forth. Reverse D-peptides desirably retain the same tertiary conformation and therefore the same activity, as the L-amino acid peptides, but desirably are more stable to enzymatic degradation in vitro and in vivo, and therefore can have greater therapeutic efficacy than the original peptide (Brady and Dodson, Nature 368:692-693, 1994; and Jameson and McDonnel, Nature 368:744-746, 1994). Peptide mimetics also include reverse-L peptides which contain L-amino acids arranged in a reverse sequence relative to a parent peptide. The C-terminal residue of the parent peptide becomes N-terminal for the reverse-L peptide, and so forth.

The peptide mimetics of the embodiments are preferably substantially similar in both three-dimensional shape and biological activity to the peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytic degradation without adversely affecting activity. A second method is altering cyclic structure for stability, such as N to C interchain imides and lactams. An example of this is given in conformationally restricted thymopentin-like compounds, such as those disclosed in U.S. Pat. No. 4,457,489, the present disclosure of which is incorporated by reference herein in its entirety. A third method is to substitute peptide bonds in the peptide by pseudopeptide bonds that confer resistance to proteolysis.

A peptide mimetics may include protective groups at one or both ends of the mimetic, or replacement of one or more peptide bonds with non-peptide bonds, is less susceptible to proteolytic cleavage than the peptide itself. For instance, one or more peptide bonds can be replaced with an alternative type of covalent bond (e.g., a carbon-carbon bond or an acyl bond). Peptide mimetics can also incorporate amino-terminal or carboxyl terminal blocking groups such as t-butyloxycarbonyl, acetyl, alkyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl, thereby rendering the mimetic less susceptible to proteolysis. Non-peptide bonds and carboxyl- or amino-terminal blocking groups can be used singly or in combination to render the mimetic less susceptible to proteolysis than the corresponding peptide. Additionally, substitution of D-amino acids for the normal L-stereoisomer can be effected, e.g. to increase the half-life of the molecule. Accordingly, the peptide mimetics include peptides having one or more of the following modifications: peptides wherein one or more of the peptidyl [—C(O)NR—] linkages (bonds) have been replaced by a non-peptidyl linkage such as a —CH$_2$-carbamate linkage [—CH$_2$—OC(O)NR—]; a phosphonate linkage; a —CH$_2$-sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$— where R$^6$ is lower alkyl]; peptides wherein the N-terminus is derivatized to a —NRR$^1$ group; to a —NRC(O)R group; to a —NRC(O)OR group; to a —NRS(O)$_2$R group; to a —NHC(O)NHR group, where R and R$^1$ are hydrogen or lower alkyl with the proviso that R and R$^1$ are not both hydrogen; to a succinimide group; to a benzyloxycarbonyl-NH—(CBZ—CH—) group; or to a benzyloxycarbonyl-NE- group having from 1 to 3 substituents on the phenyl ring selected from the group consisting of lower alkyl, lower alkoxy, chloro, and bromo; or peptides wherein the C terminus is derivatized to —C(O)R$^2$ where R$^2$ is selected from the group consisting of lower alkoxy, and —NR$^3$R$^4$ where R$^3$ and R$^4$ are independently selected from the group consisting of hydrogen and lower alkyl.

Preferred mimetics have from zero to all of the —C(O)NH— linkages of the peptide replaced by a linkage selected from the group consisting of a —CR$_2$OC(O)NR—linkage; a phosphonate linkage; a —CH$_2$S(O)$_2$NR— linkage; a —CH$_2$NR— linkage; and a —C(O)NR$^6$— linkage, and a —NHC(O)NH— linkage where R is hydrogen or lower alkyl and R$^6$ is lower alkyl, and wherein the N-terminus of the mimetic is selected from the group consisting of a —NRR¹ group; a —NRC(O)R group; a —NRC(O)OR group; a —NRS(O)₂R group; a —NHC(O)NHR group; a succinimide group; a benzyloxycarbonyl-NH— group; and a benzyloxycarbonyl-NH— group having from 1 to 3 substituents on the phenyl ring selected from the group consisting of lower alkyl, lower alkoxy, chloro, and bromo, where R and R¹ are independently selected from the group consisting of hydrogen and lower alkyl, and still further wherein the C-terminus of the mimetic has the formula —C(O)R² where R² is selected from the group consisting of hydroxy, lower alkoxy, and —NR³R⁴ where R³ and R⁴ are independently selected from the group consisting of hydrogen and lower alkyl and where the nitrogen atom of the —NR³R⁴ group can optionally be the amine group of the N-terminus of the peptide so as to form a cyclic peptide, and physiologically acceptable salts thereof.

The term "fragment" or "subsequence" refers to a protein or polypeptide that consists of a continuous subsequence of the amino acid sequence of a protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker. Such fragments may comprise at least 3 contiguous amino acids that are identical to the amino acid sequence of the present disclosure.

The phrase "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences) for use in animals, and more particularly in humans.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

Iron Metabolism Diseases

Conditions that may be treated and/or prevented using the fusion proteins or variants, derivatives, fragments or peptide mimetics derived therefrom of the present disclosure include any disease, disorder, or syndrome associated with perturbations in iron metabolism. Perturbations in iron metabolism may be associated with disturbances in one or more of iron uptake, iron absorption, iron transport, iron storage, iron processing, iron mobilization, and iron utilization. Generally, perturbations in iron metabolism result in iron overload, iron maldistribution or iron deficiency.

Conditions associated with iron overload include both primary and secondary iron overload diseases, syndromes or disorders, including, but not limited to, hereditary hemochromatosis, porphyria cutanea tarda, hereditary spherocytosis, hypochromic anemia, hypererythropoietic anemia (CDAI), faciogenital dysplasia (FGDY), Aarskog syndrome, atransferrinemia, sideroblastic anemia (SA), pyridoxine-responsive sideroblastic anemia, and hemoglobinopathies such as thalassemia and sickle cell. Some studies have suggested an association between iron metabolism disorders, such as thalassemia and hemochromatosis, and a number of disease states, such as type II (non-insulin dependent) diabetes mellitus and atherosclerosis (A. J. Matthews et al., J. Surg. Res., 1997, 73: 3540; T. P. Tuomainen et al., Diabetes Care, 1997, 20: 426-428).

Diseases associated with iron deficiency and/or iron maldistribution include, but are not limited to, anemia of chronic disease, anemia of inflammation, iron deficiency anemias, functional iron deficiency, and microcytic anemia. The terms "anemia of chronic disease" or "anemia of inflammation" refer to any anemia that develops as a result of, for example, extended infection, inflammation, neoplastic disorders, etc. The anemia which develops is often characterized by a shortened red blood cell life span and sequestration of iron in macrophages, which results in a decrease in the amount of iron available to make new red blood cells. Conditions associated with anemia of chronic disease or anemia of inflammation include, but are not limited to, chronic kidney disease, end stage renal disease, neoplastic disorders, chronic bacterial endocarditis, osteomyelitis, rheumatic fever, and ulcerative colitis. Further conditions include other diseases and disorders associated with infection, inflammation, and neoplasms, including, for example, inflammatory infections (e.g., pulmonary abscess, tuberculosis, etc), inflammatory noninfectious disorders (e.g., rheumatoid arthritis, systemic lupus erythrematosus, Crohn's disease, hepatitis, inflammatory bowel disease, etc.), and various cancers, tumors, and malignancies (e.g., carcinoma, sarcoma, lymphoma, etc.). Iron deficiency anemia may result from conditions such as pregnancy, menstruation, infancy and childhood, blood loss due to injury, etc.

It has also been suggested that iron metabolism plays a role in a number of other diseases states, including cardiovascular disease (e.g. congestive heart failure), Alzheimer's disease, Parkinson's disease, and certain types of colorectal cancers (see, for example, P. Tuomainen et al., Circulation, 1997, 97: 1461-1466; J. M. McCord, Circulation, 1991, 83: 1112-1114; J. L. Sullivan, J. Clin. Epidemiol., 1996, 49: 1345-1352; M. A. Smith et al., Proc. Nat. Acad. Sci., 1997, 94: 9866-9868; P. Riederer et al., J. Neurochem., 1989, 512: 515-520; P. Knekt et al., Int. J. Cancer, 1994, 56: 379-382).

Cancer

It has been shown that gene expression profiles in breast cancers from >800 women reveal that decreased ferroportin gene expression is associated with a significant reduction in metastasis-free and disease-specific survival that is independent of other breast cancer risk factors. (Pinnix et al. Science Translational Medicine 2(43):1-10 (August 2010)). High ferroportin and low hepcidin gene expression identified an extremely favorable cohort of breast cancer patients who have a 10-year survival of >90%. Thus, administering HJV.Fc to lower BMP signaling and thus hepcidin gene expression and to elevate ferroportin levels in cancer patients, including but not limited to breast cancer patients, should achieve a significant reduction in metastasis-free and disease-specific survival.

Pharmaceutical Compositions

The present disclosure relates to a method for therapy, prevention and amelioration of iron homeostasis disorders. The fusion proteins and variants, derivatives, fragments and peptide mimetics derived therefrom of the present disclosure are useful in the treatment of conditions or diseases associated with iron homeostasis.

Therefore, methods of the present disclosure comprise administering to a subject in need thereof or at risk of being in need thereof an effective amount of one or more of the fusion proteins or variants, derivatives, fragments and peptide mimetics derived therefrom of the present disclosure, or a composition comprising one or more of the fusion proteins or variants, derivatives, fragments and peptide mimetics derived therefrom of the present disclosure to a subject, to mobilize iron and increase serum hemoglobin and/or hematocrit levels. In one embodiment, an effective amount of a therapeutic composition comprising one or more of the fusion proteins or variants, derivatives, fragments and peptide mimetics derived therefrom of the present disclosure and a suitable pharmaceutical carrier is administered to a subject to mobilize iron and increase serum hemoglobin and/or hematocrit levels to prevent or ameliorate symptoms or treat a disorder, disease or condition related to iron homeostasis. In one embodiment, the subject is an animal. In another embodiment, the subject is a mammal, and preferably a human.

The fusion proteins or variants, derivatives, fragments and peptide mimetics derived therefrom of the present disclosure are used in the treatment, prophylaxis or amelioration of symptoms in any disease condition or disorder where the mobilization of iron and increase in serum hemoglobin and/or hematocrit levels might be beneficial.

Compositions within the scope of the present disclosure should contain the active agent (e.g. one or more of the fusion proteins or variants, derivatives, fragments and peptide mimetics derived therefrom of the present disclosure) in an amount effective to achieve the desired therapeutic effect while avoiding adverse side effects. Pharmaceutically acceptable preparations and salts of the active agent are within the scope of the present disclosure and are well known in the art. For the administration of polypeptide antagonists and the like, the amount administered should be chosen so as to avoid adverse side effects. The amount of the therapeutic or pharmaceutical composition which is effective in the treatment of a particular disease, disorder or condition will depend on the nature and severity of the disease, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 100 mg/kg are administered to the subject twice a week. Preferably, 10 to 30 mg/kg are administered to the subject twice a week. In one specific embodiment, 20 mg/kg are administered to the subject twice a week. Effective doses may be extrapolated from dose response curves derived from in vitro or animal model test systems. For example, in order to obtain an effective mg/kg dose for humans based on data generated from rat studies, the effective mg/kg dosage in rat is divided by six.

Various delivery systems are known and can be used to administer the fusion proteins or variants, derivatives, fragments and peptide mimetics derived therefrom or a pharmaceutical composition containing these fusion proteins or variants, derivatives, fragments and peptide mimetics derived therefrom of the present disclosure. The pharmaceutical composition of the present disclosure can be administered by any suitable route including, intravenous or intramuscular injection, intraventricular or intrathecal injection (for central nervous system administration), orally, topically, subcutaneously, subconjunctivally, or via intranasal, intradermal, sublingual, vaginal, rectal or epidural routes. The preferred route of administration is intravenous administration.

Other delivery systems well known in the art can be used for delivery of the pharmaceutical compositions of the present disclosure, for example via aqueous solutions, encapsulation in microparticles, or microcapsules.

In yet another embodiment, the pharmaceutical compositions of the present disclosure can be delivered in a controlled release system. In one embodiment polymeric materials can be used, in another embodiment, a pump may be used.

As mentioned above, pharmaceutical compositions of the present disclosure comprise one or more of the fusion proteins or variants, derivatives, fragments and peptide mimetics derived therefrom of the present disclosure combined with a pharmaceutically acceptable carrier. The term carrier refers to diluents, adjuvants and/or excipients such as fillers, binders, disintegrating agents, lubricants, silica flow conditioner, stabilizing agents or vehicles with which the peptide, peptide derivative or peptidomimetic is administered. Such pharmaceutical carriers include sterile liquids such as water and oils including mineral oil, vegetable oil (e.g., peanut oil, soybean oil, sesame oil and canola oil), animal oil or oil of synthetic origin. Aqueous glycerol and dextrose solutions as well as saline solutions may also be employed as liquid carriers of the pharmaceutical compositions of the present disclosure. Of course, the choice of the carrier depends on the nature of the peptide, peptide derivative or peptidomimetic, its solubility and other physiological properties as well as the target site of delivery and application. Examples of suitable pharmaceutical carriers are described in Remington: The Science and Practice of Pharmacy by Alfonso R. Gennaro, 2003, 21st edition, Mack Publishing Company.

Further pharmaceutically suitable materials that may be incorporated in pharmaceutical preparations of the present disclosure include absorption enhancers, pH regulators and buffers, osmolarity adjusters, preservatives, stabilizers, antioxidants, surfactants, thickeners, emollient, dispersing agents, flavoring agents, coloring agents and wetting agents.

Examples of suitable pharmaceutical excipients include, water, glucose, sucrose, lactose, glycol, ethanol, glycerol monostearate, gelatin, rice, starch, flour, chalk, sodium stearate, malt, sodium chloride and the like. The pharmaceutical compositions of the present disclosure can take the form of solutions, capsules, tablets, creams, gels, powders, sustained release formulations and the like. The composition can be formulated as a suppository, with traditional binders and carriers such as triglycerides (see Remington: The Science and Practice of Pharmacy by Alfonso R. Gennaro, 2003, 21.sup.th edition, Mack Publishing Company). Such compositions contain a therapeutically effective amount of the therapeutic composition, together with a suitable amount of carrier so as to provide the form for proper administration to the subject. The formulations are designed so as to suit the mode of administration and the target site of action (e.g., a particular organ or cell type).

The pharmaceutical compositions of the present disclosure can be formulated as neutral or salt forms. Pharmaceutically acceptable salts include those that form with free amino groups and those that react with free carboxyl groups. Non-toxic alkali metal, alkaline earth metal and ammonium salts commonly used in the pharmaceutical industry include sodium, potassium, lithium, calcium, magnesium, barium, ammonium, and protamine zinc salts, which are prepared by methods well known in the art. The term also includes non-toxic acid addition salts, which are generally prepared by reacting the compounds of the present disclosure with suitable organic or inorganic acid. Representative salts include the hydrobromide, hydrochloride, valerate, oxalate, oleate, laureate, borate, benzoate, sulfate, bisulfate, acetate, phosphate, tysolate, citrate, maleate, fumarate, tartrate, succinate, napsylate salts and the like.

Examples of fillers or binders that may be used in accordance with the present disclosure include acacia, alginic acid, calcium phosphate (dibasic), carboxymethylcellulose, carboxymethylcellulose sodium, hydroxyethylcellulose, hydroxypropylcellulose, hydroxypropylmethylcellulose, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth, microcrystalline cellulose, starch, and zein. Another most preferred filler or binder consists of microcrystalline cellulose.

Examples of disintegrating agents that may be used include alginic acid, carboxymethylcellulose, carboxymethylcellulose sodium, hydroxypropylcellulose (low substituted), microcrystalline cellulose, powdered cellulose, colloidal silicon dioxide, sodium croscarmellose, crospovidone, methylcellulose, polacrilin potassium, povidone, sodium alginate, sodium starch glycolate, starch, disodium disulfite, disodium edathamil, disodium edetate, disodiumethylenediaminetetraacetate (EDTA) crosslinked polyvinylpyrollidines, pregelatinized starch, carboxymethyl starch, sodium carboxymethyl starch and microcrystalline cellulose.

Examples of lubricants include calcium stearate, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc, zinc stearate, glyceryl behapate, magnesium lauryl sulfate, boric acid, sodium benzoate, sodium acetate, sodium benzoate/sodium acetate (in combination) and DL leucine.

Examples of silica flow conditioners include colloidal silicon dioxide, magnesium aluminum silicate and guar gum. Another most preferred silica flow conditioner consists of silicon dioxide.

Examples of stabilizing agents include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol.

The present disclosure also provides for modifications of peptides or peptide derivatives such that they are more stable once administered to a subject (i.e., once administered it has a longer half-life or longer period of effectiveness as compared to the unmodified form). Such modifications are well known to those skilled in the art to which this disclosure pertain (e.g., polyethylene glycol derivatization a.k.a. PEGylation, microencapsulation, etc.).

Methods of Screening

The present disclosure provides for methods of screening for compounds (e.g., HJV-IgG fusion proteins and variants, derivatives and peptide mimetics derived therefrom.) that alter serum iron, serum hemoglobin and/or hematocrit levels in mammalian subjects. According to some embodiments, there is provided a method for screening for compounds that mobilize iron and serum hemoglobin and/or hematocrit levels in mammalian subjects (e.g., increased or decreased).

In another embodiment, the present disclosure provides methods of screening for compounds, wherein the compounds are screened for their ability to specifically bind to BMP-6. In specific embodiments, compositions of the present disclosure are screened for their ability of bind to BMP-6 with a $K_D$ of at least $10^{-5}$, $10^{-6}$, $10^{-7}$, $10^{-8}$, $10^{-9}$, $10^{\times 10}$, $10^{-11}$ or $10^{-12}$ M. In another embodiment, the present disclosure provides methods of screening for compounds, wherein the compounds are screened for their ability to inhibit BMP-6 signaling. In specific embodiments, compositions of the present disclosure are screened for their ability to inhibit BMP-6 signaling by at least 10, 20, 30, 40, 50, 60, 70, 80, 90, 95, 97, 99 or 100%.

Recombinant Expression Vectors and Host Cells

Another aspect of the present disclosure pertains to vectors, preferably expression vectors, containing a nucleic acid encoding fusion proteins and variants, derivatives and peptide mimetics derived therefrom of the present disclosure. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the present disclosure is intended to include such other forms of expression vectors, such as viral vectors (e.g., replication defective retroviruses, adenoviruses and adeno associated viruses), which serve equivalent functions.

The recombinant expression vectors of the present disclosure comprise a nucleic acid of the present disclosure in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue specific regulatory sequences). It will be appreciated by those skilled in the art that the design of the expression vector can depend on such factors as the choice of the host cell to be transformed, the level of expression of protein desired, etc. The expression vectors of the present disclosure can be introduced into host cells to thereby produce fusion proteins and variants, derivatives and peptide mimetics derived therefrom of the present disclosure, encoded by nucleic acids as described herein.

The recombinant expression vectors of the present disclosure can be designed for expression of fusion proteins and variants, derivatives and peptide mimetics derived therefrom of the present disclosure in prokaryotic or eukaryotic cells. For example, fusion proteins and variants, derivatives and peptide mimetics derived therefrom of the present disclosure can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31 40), pMAL (New England Biolabs, Beverly, Mass.) and pRIT5 (Pharmacia, Piscataway, N.J.) that fuse glutathione S transferase (GST), maltose E binding protein, or protein A, respectively, to the target recombinant protein.

Examples of suitable inducible non fusion E. coli expression vectors include pTrc (Amrann et al., (1988) Gene 69:301 315) and pET lld (Studier et al., GENE EXPRESSION TECHNOLOGY: METHODS IN ENZYMOLOGY 185, Academic Press, San Diego, Calif. (1990) 60 89).

One strategy to maximize recombinant protein expression in E. coli is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119 128. Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:211:1-7, 10-13, 19-34, 45-53, 58-85, 111-113, 120, 130, 132-134 and 13518). Such alteration of nucleic acid sequences of the present disclosure can be carried out by standard DNA synthesis techniques.

In another embodiment, the expression vector used with the compositions of the present disclosure is a yeast expression vector. Examples of vectors for expression in yeast S. cerevisiae include pYepSecl (Baldari, et al., (1987) EMBO J 6:229 234), pMFa (Kurjan and Herskowitz, (1982) Cell 30:933 943), pJRY88 (Schultz et al., (1987) Gene 54:113 123), pYES2 (Invitrogen Corporation, San Diego, Calif.), and picZ (InVitrogen Corp, San Diego, Calif.).

Alternatively, the compositions of the present disclosure can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156 2165) and the pVL series (Lucklow and Summers (1989) Virology 170:31 39).

In yet another embodiment, a nucleic acid of the present disclosure is expressed in mammalian cells using a mammalian expression vector. Examples of mammalian expression vectors include pCDM8 (Seed (1987) Nature 329:840) and pMT2PC (Kaufman et al. (1987) EMBO J 6: 187 195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue specific regulatory elements are used to express the nucleic acid). Tissue specific regulatory elements are known in the art. Non limiting examples of suitable tissue specific promoters include the albumin promoter (liver specific; Pinkert et al. (1987) Genes Dev 1:268 277), lymphoid specific promoters (Calame and Eaton (1988) Adv Immunol 43:235 275), in particular promoters of T cell receptors (Winoto and Baltimore (1989) EMBO J 8:729 733) and immunoglobulins (Banerji et al. (1983) Cell 33:729 740; Queen and Baltimore (1983) Cell 33:741 748), neuron specific promoters (e.g., the neurofilament promoter; Byrne and Ruddle (1989) PNAS 86:5473 5477), pancreas specific promoters (Edlund et al. (1985) Science 230:912 916), and mammary gland specific promoters (e.g., milk whey promoter; U.S. Pat. No. 4,873,316 and European Application Publication No. 264, 166). Developmentally regulated promoters are also encompassed, e.g., the murine hox promoters (Kessel and Gruss (1990) Science 249:374 379) and the α-fetoprotein promoter (Campes and Tilghman (1989) Genes Dev 3:537 546).

The present disclosure further provides a recombinant expression vector comprising a DNA molecule of the present disclosure cloned into the expression vector in an antisense orientation. That is, the DNA molecule is operatively linked to a regulatory sequence in a manner that allows for expression (by transcription of the DNA molecule) of an RNA molecule that is antisense to the mRNA of the fusion protein of the present disclosure. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews: Trends in Genetics, Vol. 1(1) 1986.

Another aspect of the present disclosure pertains to host cells into which a recombinant expression vector of the present disclosure has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, fusion proteins and variants, derivatives and peptide mimetics derived therefrom of the present disclosure can be expressed in bacterial cells such as E. coli, insect cells, yeast or mammalian cells (such as Chinese hamster ovary cells (CHO) or COS cells). Other suitable host cells are known to those skilled in the art. In a preferred embodiment, the fusion protein or variant, derivative or peptide mimetic derived therefrom of the present disclosure is expressed in CHO cells.

Vector DNA can be introduced into prokaryotic or eukaryotic cells via conventional transformation or transfection techniques. As used herein, the terms "transformation" and "transfection" are intended to refer to a variety of art recognized techniques for introducing foreign nucleic acid (e.g., DNA) into a host cell, including calcium phosphate or calcium chloride co precipitation, DEAE dextran mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the composition of the present disclosure or can be introduced on a separate vector. Cells stably transfected with the introduced nucleic acid can be identified by drug selection (e.g., cells that have incorporated the selectable marker gene will survive, while the other cells die).

A host cell of the present disclosure, such as a prokaryotic or eukaryotic host cell in culture, can be used to produce (i.e., express) one or more fusion proteins and variants, derivatives and peptide mimetics derived therefrom of the present disclosure. Accordingly, the present disclosure further provides methods for producing one or more fusion proteins and variants, derivatives and peptide mimetics derived therefrom of the present disclosure using the host cells of the present disclosure. In one embodiment, the method comprises culturing the host cell of disclosure (into which a recombinant expression vector encoding a composition of the present disclosure has been introduced) in a suitable medium such that the composition of the present disclosure is produced. In another embodiment, the method further comprises isolating the composition of the present disclosure from the medium or the host cell.

Without further elaboration, it is believed that one skilled in the art can, using the preceding description, utilize the present disclosure to its fullest extent. The following examples are illustrative only, and not limiting of the remainder of the present disclosure in any way whatsoever.

EXAMPLES

Example 1. Increase in Hematocrit in Anemic Rats Treated with a Hemojuvelin-Fc Fusion Protein Rats were injection with a dose of rhamnose at 15 mg/kg. After 28 days, rats that developed joint swelling, anemia and marked leukocytosis were randomly assigned to one of three groups. In group 1, rats were treated with intravenous injections of HJV.Fc (SEQ ID NO:9) at 2 mg/kg twice weekly for 4 weeks. In group 2, rats were treated with intravenous injections of HJV.Fc at 20 mg/kg twice weekly for 4 weeks. Group 3 rats were untreated.

Weekly hematocrit and hemoglobin serum concentrations were measured. At the terminal bleed at the end of four weeks, hematocrit, hemoglobin, serum iron, splenic ferritin and liver hepcidin RNA was determined.

Figure 3:
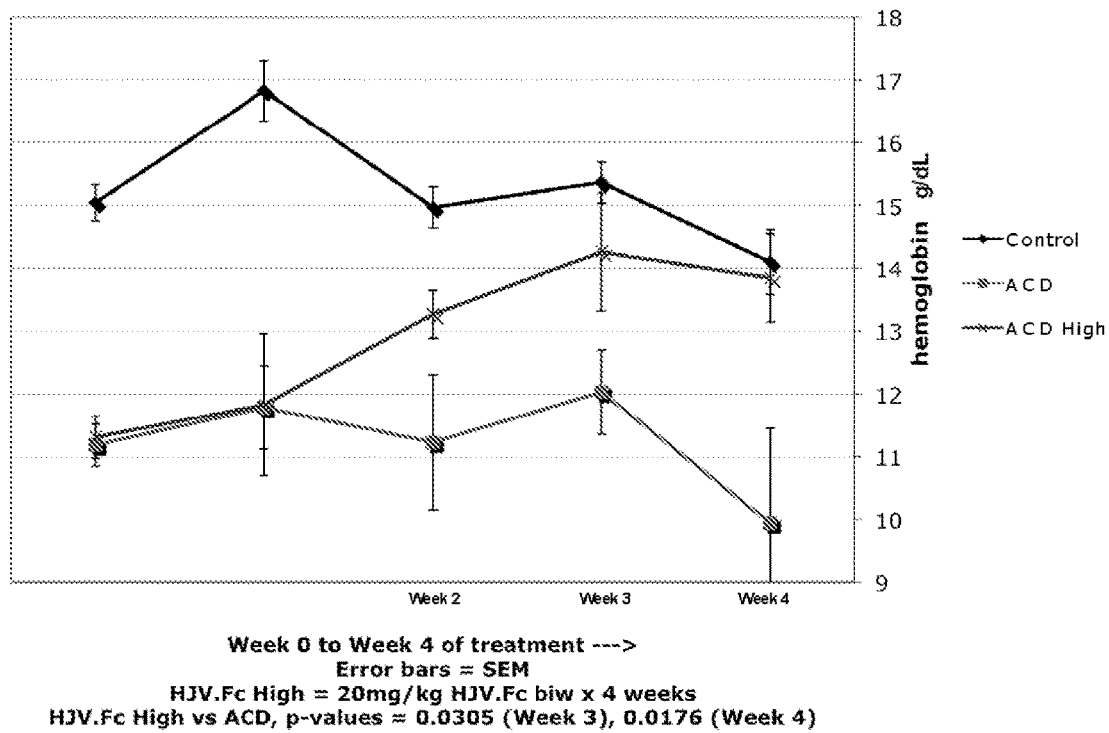
FIG. 3 is a line graph showing serum hemoglobin levels in anemic rats administered 20 mg/kg of HJV.Fc compared to control rats.
Figure 4:
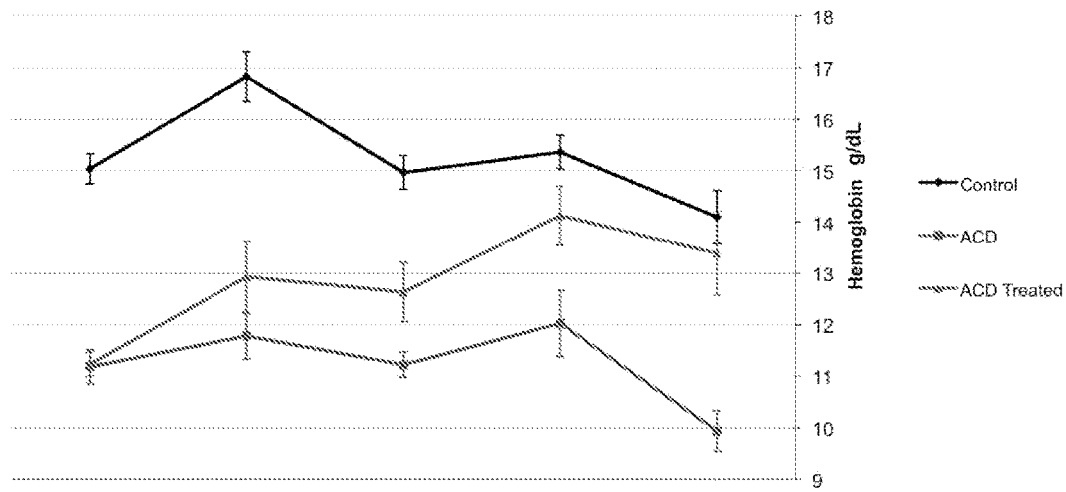
FIG. 4 is a line graph showing serum hemoglobin levels in anemic rats administered 2 or 20 mg/kg of HJV.Fc compared to control rats.
Figure 5:
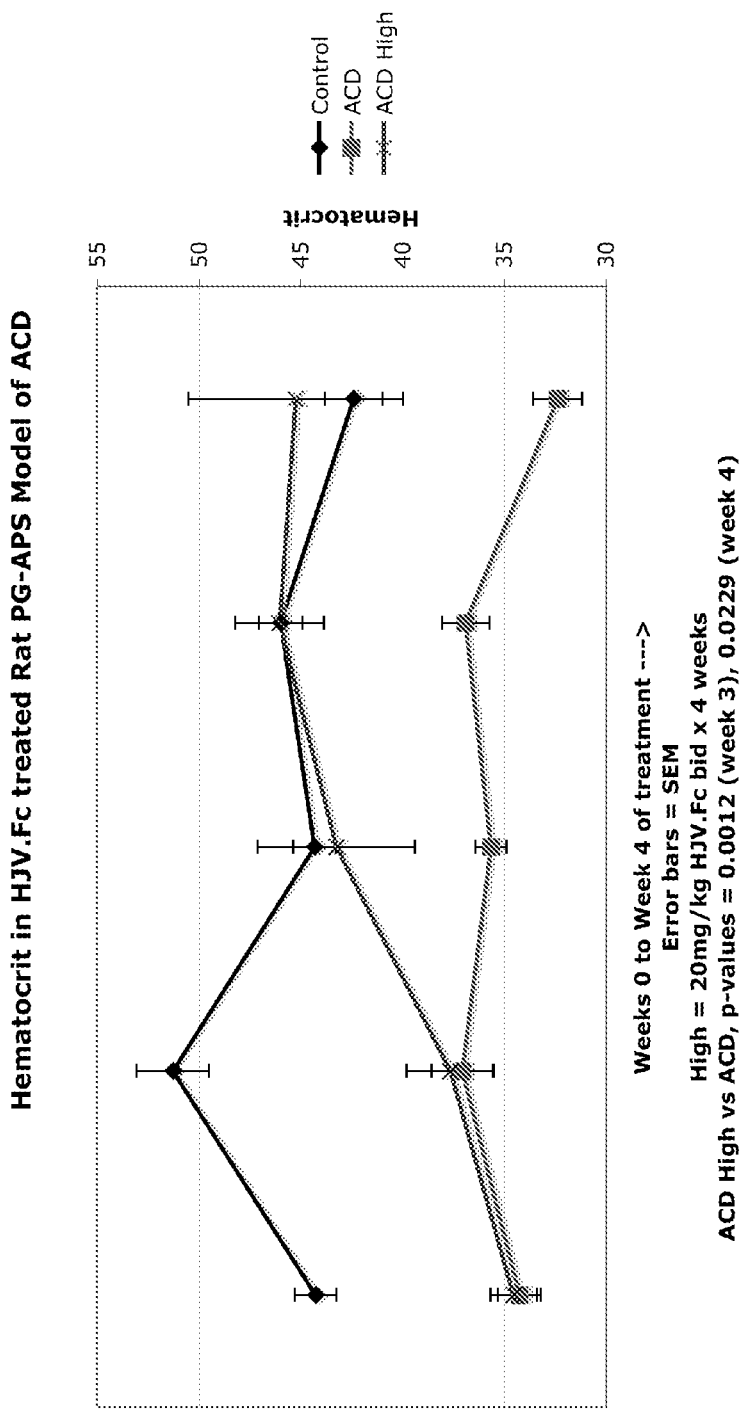
FIG. 5 is a bar graph that shows hematocrit levels in anemic rats administered 20 mg/kg of HJV.Fc compared to control rats.
Figure 6:
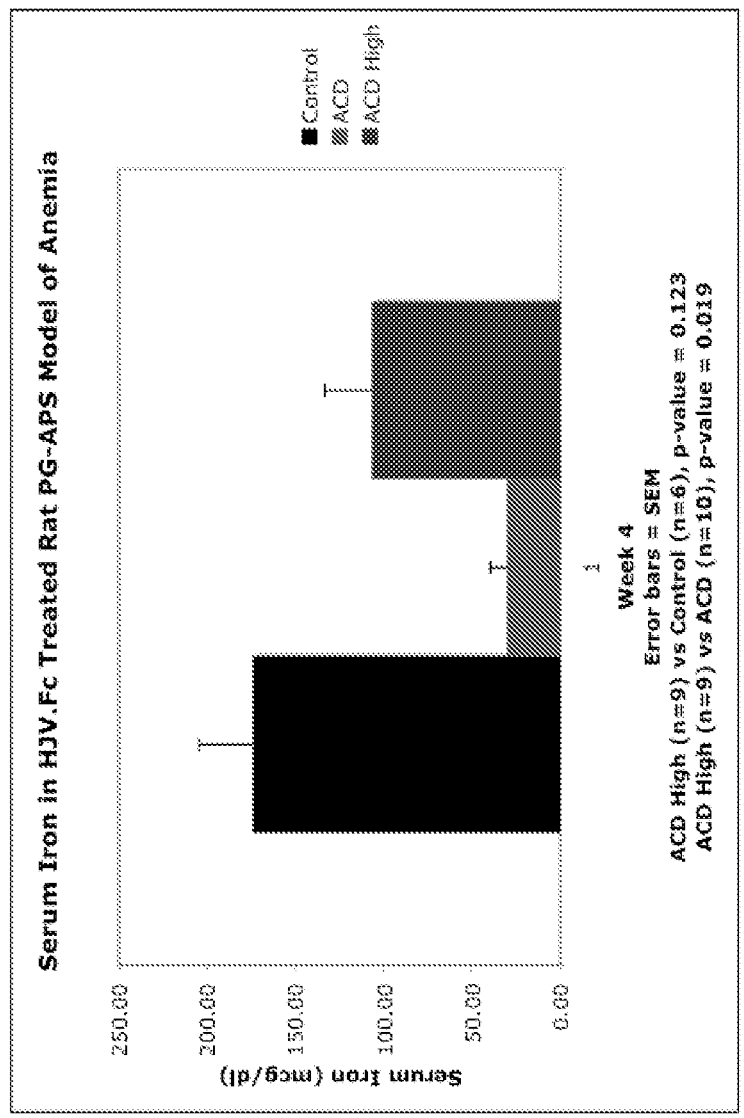
FIG. 6 is a bar graph showing serum iron in anemic rats administered 20 mg/kg of HJV.Fc compared to control rats.

As shown in FIGS. 3, 5 and 6, anemic rats administered the high dose of HJV.Fc had significantly higher serum hematocrit and serum hemoglobin than anemic rats not administered HJV.Fc. Anemic rats administered HJV.Fc had serum hematocrit and hemoglobin similar to non-anemic rats at the end of four weeks of treatment. When data from the low dose HJV.Fc was added to the high dose data, rats administered HJV.Fc had significantly higher serum hematocrit and serum hemoglobin than anemic rats not administered HJV.Fc (FIG. 4). Again, anemic rats administered HJV.Fc had serum hematocrit and hemoglobin similar to non-anemic rats at the end of four weeks of treatment.

Example 2. Monomeric HJV.His has Low Affinity to BMP-6

Figure 7A:
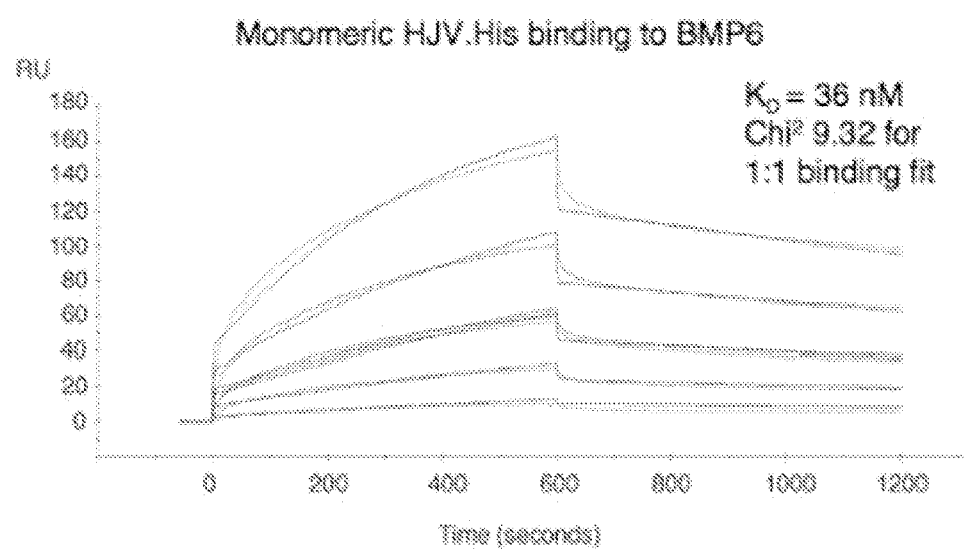
FIG. 7A is a graph showing HJV.His (homodimer) affinity using data from Biacore binding assay to BMP6.
Figure 7B:
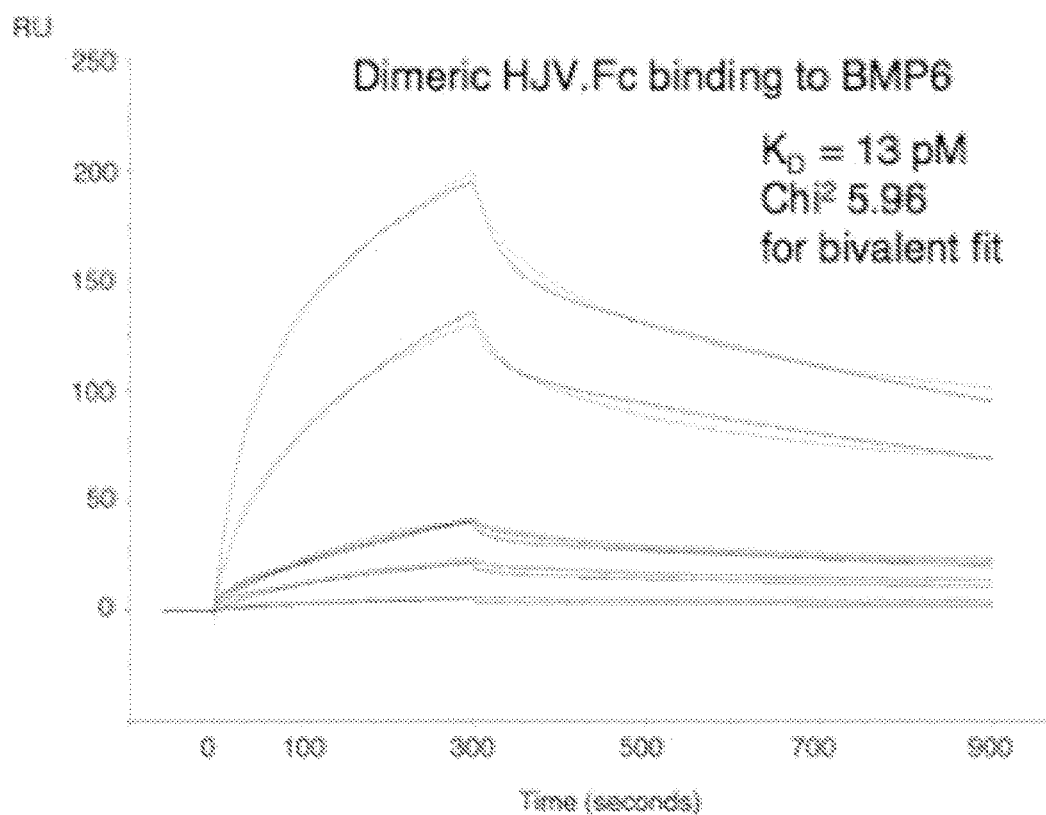
FIG. 7B is a graph showing HJV.Fc (homodimer) affinity using data from Biacore binding assay to BMP6.

FIG. 7a shows the binding of soluble human hemojuvelin with a HIS-tag binding to human BMP6 immobilized on CM5 sensor chips by the amine coupling method (Halbrooks 2007). Using a one-site univalent fit model, an approximate $K_d$ of 33 nM is obtained. FIG. 7b, shows that soluble HJV.Fc protein can also bind to immobilized human BMP6, and that a two-site bivalent fit model (to account for the disulfide bonded dimeric nature of HJV.Fc) gives a preliminary $K_d$ of approximately 13 pM, which is a much higher affinity compared to monomeric HJV.His protein. Thus, as shown in FIG. 7a, monomeric HJV.His has low affinity to BMP6. In FIG. 7b, homodimeric HJV.Fc has a significantly higher binding affinity to BMP6.

Example 3. HJV.Fc can Inhibit BMP6 Activity in a Dose-Dependent Manner

Figure 8:
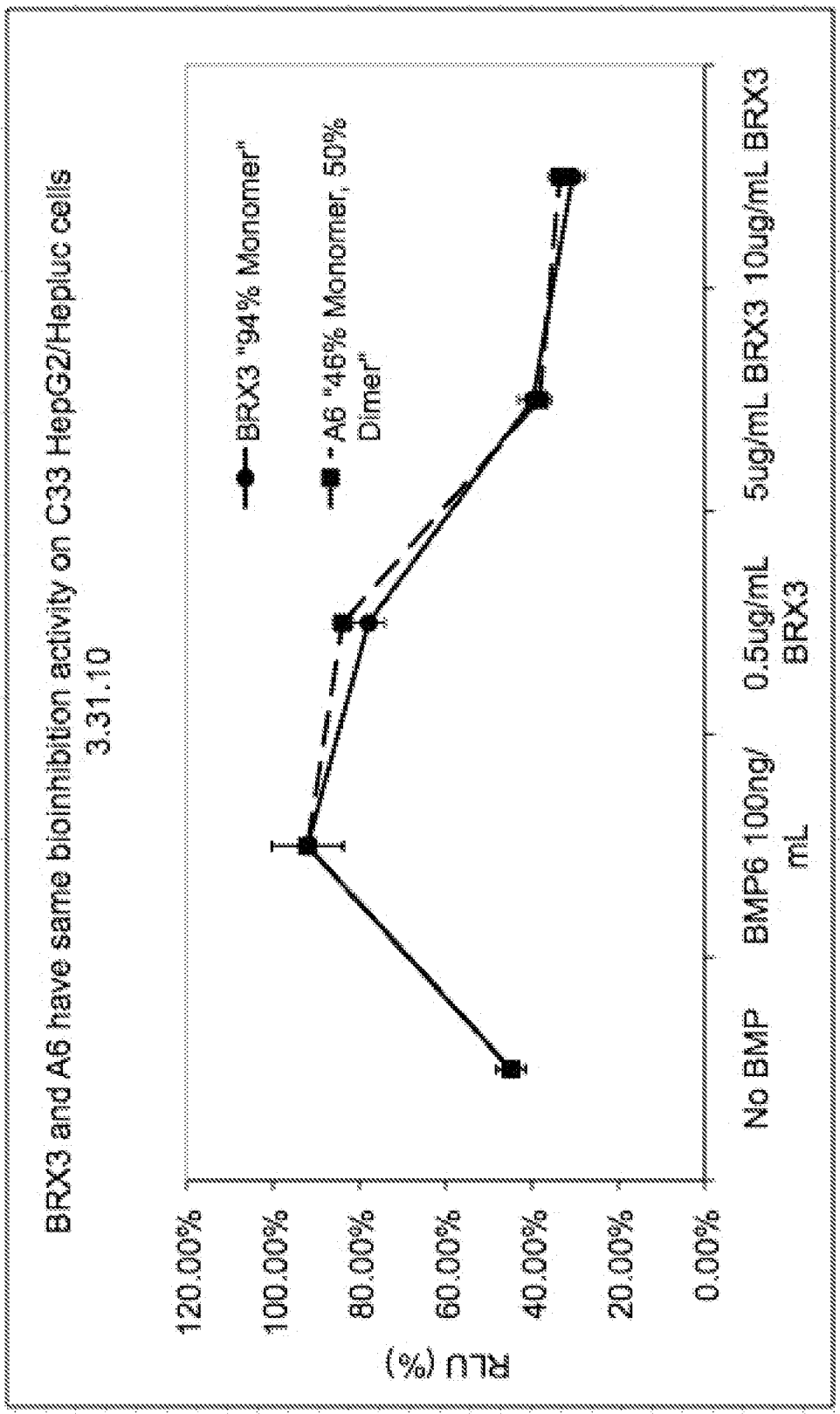
FIG. 8 shows HJV.Fc is effective in inhibiting BMP6 activity in a cell-based bioinhibition assay.
Figure 9:
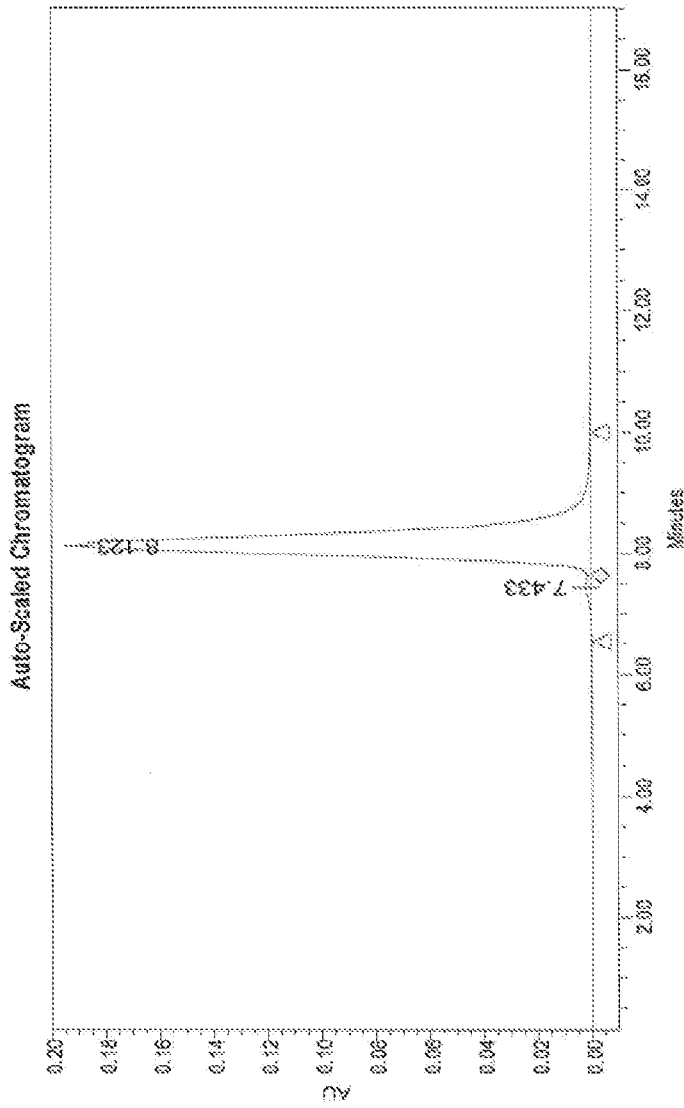
FIG. 9 shows a preparation of >95% purity of monomers of the homodimeric HJV.Fc by HPLC analysis.

As shown in FIG. 8, using a cell-based bioinhibition luciferase assay, HJV.Fc can inhibit BMP6 activity in a dose-dependent manner. Hepcidin promoter luciferase assays in a hepatoma-derived HepG2 cells were carried out as previously described (Babitt 2007). For HJV.Fc inhibition assays, HepG2 cells stably transfected with the hepcidin promoter luciferase reporter (cell line C33) were serum starved for 6 hours and then incubated with 100 ng/ml BMP-6 ligand, either alone or with 0.5, 5 or 10 µg/ml of HJV.Fc for 16 hours. "BRX3" and "A6" are two different lots of HJV.Fc proteins. Moreover, as shown in FIG. 9, HJV.Fc can be prepared in an essentially pure preparation of the homodimeric protein as demonstrated by HPLC analysis. This analytical method involved the injection of a sample of HJV.Fc on to a BioSep 53000 chromatography column (Phenomenex) with a running buffer of 100 mM Sodium Phosphate, 200 mM Sodium Chloride, at pH 6.0. The flow rate was 1 ml/min and detection was achieved at a wavelength of 280 nm.

All publications and patent applications cited in this specification are herein incorporated by reference as if each individual publication or patent application are specifically and individually indicated to be incorporated by reference.

Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

The invention claimed is:

1. A composition comprising a fusion protein wherein the fusion protein comprises the sequence of SEQ ID NO:9.

2. The composition of claim 1, wherein the fusion protein is at least 98% pure as determined by size exclusion chromatography.

3. The composition of claim 1, wherein the fusion protein is glycosylated.

4. The composition of claim 3, wherein the glycosylation pattern is a mammalian glycosylation pattern.

5. The composition of claim 4, wherein asparagine 83, asparagine 178 and/or asparagine 337 are glycosylated.

6. The composition of claim 4, wherein the glycosylation pattern is from a Chinese hamster ovary (CHO) cell line.

7. The composition of claim 1, wherein the N-terminal amino acid of the fusion protein is glutamine.

8. The composition of claim 7, wherein the N-terminus of the N-terminal amino acid of the fusion is QCKILRCNAE (SEQ ID NO: 10).

9. The composition of claim 1, wherein the composition is substantially pyrogen free.

10. The composition of claim 1, wherein the serum half-life of the fusion protein is at least 10 hours.

11. The composition of claim 1, wherein the fusion protein binds to bone morphogenic protein-6 ("BMP-6") with a KD of at least $10^{-7}$M and inhibits BMP-6 signaling.

12. The composition of claim 1, wherein the composition increases hemoglobin and/or hematocrit in a subject when administered.

13. The composition of claim 1, wherein the composition increases hemoglobin and/or hematocrit to at least normal levels in an anemic subject when administered to the anemic subject for one month or more.

14. The composition of claim 1, wherein the fusion protein forms a homodimer.

15. The composition of claim 14, wherein the homodimer is formed in the Fc hinge regions.

16. The composition of claim 15, wherein the homodimer is formed between cysteines in the Fc hinge regions via a disulfide bond.

17. A nucleic acid molecule that encodes the fusion polypeptide of claim 1.

18. The nucleic acid molecule of claim 17, wherein the nucleic acid molecule encodes the fusion protein of claim 1 and comprises the sequence of SEQ ID NO: 11.

19. A mammalian cell comprising the nucleic acid sequence of claim 18.

20. The mammalian cell of claim 19, wherein the cell is a CHO cell.

21. A method of increasing serum iron levels in a subject in need thereof by administering a therapeutically effective amount of the composition of claim 1 to the subject, thereby increasing serum iron levels.

22. A composition comprising a fusion protein, wherein the fusion protein comprises an N-terminal polypeptide and a C-terminal polypeptide, wherein the N-terminal polypeptide comprises the sequence of SEQ ID NO: 1 and wherein the C-terminal peptide comprises a sequence selected from the group consisting of SEQ ID NOs: 3, 4, 5, 6, and 7.

23. The composition of claim 22, wherein the fusion protein is at least 98% pure as determined by size exclusion chromatography.

24. The composition of claim 22, wherein the fusion protein is glycosylated.

25. The composition of claim 24, wherein the glycosylation pattern is a mammalian glycosylation pattern.

26. The composition of claim 25, wherein the glycosylation pattern is from a Chinese hamster ovary (CHO) cell line.

27. The composition of claim 22, wherein the N-terminal amino acid of the fusion protein is glutamine.

28. The composition of claim 27, wherein the N-terminus of the N-terminal amino acid of the fusion is QCKILRCNAE (SEQ ID NO: 10).

29. The composition of claim 22, wherein the composition is substantially pyrogen free.

30. The composition of claim 22, wherein the serum half-life of the fusion protein is at least 10 hours.

31. The composition of claim 22, wherein the fusion protein binds to bone morphogenic protein-6 ("BMP-6") with a KD of at least $10^{-7}$M and inhibits BMP-6 signaling.

32. The composition of claim 22, wherein the composition increases hematocrit in a subject when administered.

33. The composition of claim 22, wherein the composition increases hematocrit to at least normal levels in an anemic subject when administered to the anemic subject for one month or more.

34. The composition of claim 22, wherein the fusion protein forms a homodimer.

35. A nucleic acid molecule that encodes the fusion protein of claim 22.

36. The nucleic acid of claim 35, wherein the nucleic acid molecule encodes the fusion protein of claim 22 and comprises the sequence of SEQ ID NO: 11.

37. A mammalian cell comprising the nucleic acid sequence of claim 35.

38. The mammalian cell of claim 37, wherein the cell is a CHO cell.

39. A method of increasing serum iron levels and/or improving anemia in a subject in need thereof by administering a therapeutically effective amount of the composition of claim 22 to the subject, thereby increasing serum iron levels and/or improving anemia.

* * * * *

UNITED STATES PATENT AND TRADEMARK OFFICE
CERTIFICATE OF CORRECTION

PATENT NO. : 9,708,379 B2  Page 1 of 1
APPLICATION NO. : 13/980666
DATED : July 18, 2017
INVENTOR(S) : Lin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this
Twenty-fifth Day of September, 2018

Andrei Iancu
*Director of the United States Patent and Trademark Office*

SEQUENCE LISTING

```
<160> NUMBER OF SEQ ID NOS: 11

<210> SEQ ID NO 1
<211> LENGTH: 360
<212> TYPE: PRT
<213> ORGANISM: Homo sapiens

<400> SEQUENCE: 1

Gln Cys Lys Ile Leu Arg Cys Asn Ala Glu Tyr Val Ser Ser Thr Leu
1               5                   10                  15

Ser Leu Arg Gly Gly Gly Ser Gly Ala Leu Arg Gly Gly Gly Gly Gly
            20                  25                  30

Gly Gly Arg Gly Gly Gly Val Gly Ser Gly Gly Leu Cys Arg Ala Leu
        35                  40                  45

Arg Ser Tyr Ala Leu Cys Thr Arg Arg Thr Ala Arg Thr Cys Arg Gly
    50                  55                  60

Asp Leu Ala Phe His Ser Ala Val His Gly Ile Glu Asp Leu Met Ile
65                  70                  75                  80

Gln His Asn Cys Ser Arg Gln Gly Pro Thr Ala Pro Pro Pro Pro Arg
                85                  90                  95

Gly Pro Ala Leu Pro Gly Ala Gly Ser Gly Leu Pro Ala Pro Asp Pro
            100                 105                 110

Cys Asp Tyr Glu Gly Arg Phe Ser Arg Leu His Gly Arg Pro Pro Gly
        115                 120                 125

Phe Leu His Cys Ala Ser Phe Gly Asp Pro His Val Arg Ser Phe His
    130                 135                 140

His His Phe His Thr Cys Arg Val Gln Gly Ala Trp Pro Leu Leu Asp
145                 150                 155                 160

Asn Asp Phe Leu Phe Val Gln Ala Thr Ser Ser Pro Met Ala Leu Gly
                165                 170                 175

Ala Asn Ala Thr Ala Thr Arg Lys Leu Thr Ile Ile Phe Lys Asn Met
            180                 185                 190

Gln Glu Cys Ile Asp Gln Lys Val Tyr Gln Ala Glu Val Asp Asn Leu
        195                 200                 205

Pro Val Ala Phe Glu Asp Gly Ser Ile Asn Gly Gly Asp Arg Pro Gly
    210                 215                 220

Gly Ser Ser Leu Ser Ile Gln Thr Ala Asn Pro Gly Asn His Val Glu
225                 230                 235                 240

Ile Gln Ala Ala Tyr Ile Gly Thr Thr Ile Ile Ile Arg Gln Thr Ala
                245                 250                 255
```

-continued

```
Gly Gln Leu Ser Phe Ser Ile Lys Val Ala Glu Asp Val Ala Met Ala
            260                 265                 270
Phe Ser Ala Glu Gln Asp Leu Gln Leu Cys Val Gly Gly Cys Pro Pro
        275                 280                 285
Ser Gln Arg Leu Ser Arg Ser Glu Arg Asn Arg Arg Gly Ala Ile Thr
    290                 295                 300
Ile Asp Thr Ala Arg Arg Leu Cys Lys Glu Gly Leu Pro Val Glu Asp
305                 310                 315                 320
Ala Tyr Phe His Ser Cys Val Phe Asp Val Leu Ile Ser Gly Asp Pro
                325                 330                 335
Asn Phe Thr Val Ala Ala Gln Ala Ala Leu Glu Asp Ala Arg Ala Phe
            340                 345                 350
Leu Pro Asp Leu Glu Lys Leu His
        355                 360

<210> SEQ ID NO 2
<211> LENGTH: 4
<212> TYPE: PRT
<213> ORGANISM: Artificial Sequence
<220> FEATURE:
<223> OTHER INFORMATION: Hinge region.
<220> FEATURE:
<221> NAME/KEY: VARIANT
<222> LOCATION: (1)..(1)
<223> OTHER INFORMATION: Xaa is Cys or Ser.
<220> FEATURE:
<221> NAME/KEY: VARIANT
<222> LOCATION: (3)..(3)
<223> OTHER INFORMATION: Xaa is Leu or Pro.
<220> FEATURE:
<221> NAME/KEY: VARIANT
<222> LOCATION: (4)..(4)
<223> OTHER INFORMATION: Xaa is Cys or Ser.

<400> SEQUENCE: 2

Xaa Pro Xaa Xaa
1

<210> SEQ ID NO 3
<211> LENGTH: 232
<212> TYPE: PRT
<213> ORGANISM: Artificial Sequence
<220> FEATURE:
<223> OTHER INFORMATION: IgG Fc derivative.

<400> SEQUENCE: 3

Asp Pro Lys Ser Cys Asp Lys Pro His Thr Cys Pro Leu Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
```

```
Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Ala Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 4
<211> LENGTH: 232
<212> TYPE: PRT
<213> ORGANISM: Homo sapiens

<400> SEQUENCE: 4

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 5
<211> LENGTH: 226
<212> TYPE: PRT
<213> ORGANISM: Artificial Sequence
```

```
<220> FEATURE:
<223> OTHER INFORMATION: Fc region from VEGF-R Fc fusion.

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 6
<211> LENGTH: 232
<212> TYPE: PRT
<213> ORGANISM: Artificial Sequence
<220> FEATURE:
<223> OTHER INFORMATION: Fc region from CTLA4 Fc fusion.

<400> SEQUENCE: 6

Glu Pro Lys Ser Ser Asp Lys Thr His Thr Ser Pro Pro Ser Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230

<210> SEQ ID NO 7
<211> LENGTH: 227
<212> TYPE: PRT
<213> ORGANISM: Artificial Sequence
<220> FEATURE:
<223> OTHER INFORMATION: Fc region from IL-1R Fc fusion.

<400> SEQUENCE: 7

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
210                 215                 220

Pro Gly Lys
225

<210> SEQ ID NO 8
<211> LENGTH: 5
<212> TYPE: PRT
<213> ORGANISM: Artificial Sequence
<220> FEATURE:
<223> OTHER INFORMATION: Linker.

<400> SEQUENCE: 8

Gly Gly Gly Gly Gly
1               5

<210> SEQ ID NO 9
<211> LENGTH: 596
<212> TYPE: PRT
<213> ORGANISM: Artificial Sequence
<220> FEATURE:
<223> OTHER INFORMATION: HJV.Fc fusion.

<400> SEQUENCE: 9

Gln Cys Lys Ile Leu Arg Cys Asn Ala Glu Tyr Val Ser Ser Thr Leu
1               5                   10                  15

Ser Leu Arg Gly Gly Ser Ser Gly Ala Leu Arg Gly Gly Gly Gly
            20                  25                  30

Gly Gly Arg Gly Gly Val Gly Ser Gly Gly Leu Cys Arg Ala Leu
            35                  40                  45

Arg Ser Tyr Ala Leu Cys Thr Arg Arg Thr Ala Arg Thr Cys Arg Gly
    50                  55                  60

Asp Leu Ala Phe His Ser Ala Val His Gly Ile Glu Asp Leu Met Ile
65                  70                  75                  80

Gln His Asn Cys Ser Arg Gln Gly Pro Thr Ala Pro Pro Pro Arg
            85                  90                  95

Gly Pro Ala Leu Pro Gly Ala Gly Ser Gly Leu Pro Ala Pro Asp Pro
            100                 105                 110

Cys Asp Tyr Glu Gly Arg Phe Ser Arg Leu His Gly Arg Pro Pro Gly
            115                 120                 125

Phe Leu His Cys Ala Ser Phe Gly Asp Pro His Val Arg Ser Phe His
    130                 135                 140

His His Phe His Thr Cys Arg Val Gln Gly Ala Trp Pro Leu Leu Asp
145                 150                 155                 160

Asn Asp Phe Leu Phe Val Gln Ala Thr Ser Ser Pro Met Ala Leu Gly
                165                 170                 175

Ala Asn Ala Thr Ala Thr Arg Lys Leu Thr Ile Ile Phe Lys Asn Met
            180                 185                 190

Gln Glu Cys Ile Asp Gln Lys Val Tyr Gln Ala Glu Val Asp Asn Leu
            195                 200                 205

Pro Val Ala Phe Glu Asp Gly Ser Ile Asn Gly Gly Asp Arg Pro Gly
    210                 215                 220

Gly Ser Ser Leu Ser Ile Gln Thr Ala Asn Pro Gly Asn His Val Glu
225                 230                 235                 240

Ile Gln Ala Ala Tyr Ile Gly Thr Thr Ile Ile Ile Arg Gln Thr Ala
                245                 250                 255

Gly Gln Leu Ser Phe Ser Ile Lys Val Ala Glu Asp Val Ala Met Ala
            260                 265                 270
```

```
Phe Ser Ala Glu Gln Asp Leu Gln Leu Cys Val Gly Gly Cys Pro Pro
            275                 280                 285

Ser Gln Arg Leu Ser Arg Ser Glu Arg Asn Arg Arg Gly Ala Ile Thr
    290                 295                 300

Ile Asp Thr Ala Arg Arg Leu Cys Lys Glu Gly Leu Pro Val Glu Asp
305                 310                 315                 320

Ala Tyr Phe His Ser Cys Val Phe Asp Val Leu Ile Ser Gly Asp Pro
                325                 330                 335

Asn Phe Thr Val Ala Ala Gln Ala Ala Leu Glu Asp Ala Arg Ala Phe
            340                 345                 350

Leu Pro Asp Leu Glu Lys Leu His Leu Phe Pro Ser Asp Pro Lys Ser
                355                 360                 365

Cys Asp Lys Pro His Thr Cys Pro Leu Cys Pro Ala Pro Glu Leu Leu
            370                 375                 380

Gly Gly Pro Ser Val Phe Leu Phe Pro Pro Lys Pro Lys Asp Thr Leu
385                 390                 395                 400

Met Ile Ser Arg Thr Pro Glu Val Thr Cys Val Val Val Asp Val Ser
                405                 410                 415

His Glu Asp Pro Glu Val Lys Phe Asn Trp Tyr Val Asp Gly Val Glu
            420                 425                 430

Val His Asn Ala Lys Thr Lys Pro Arg Glu Glu Gln Tyr Asn Ser Thr
        435                 440                 445

Tyr Arg Val Val Ser Val Leu Thr Val Leu His Gln Asp Trp Leu Asn
    450                 455                 460

Gly Lys Glu Tyr Lys Cys Lys Val Ser Asn Lys Ala Leu Pro Ala Pro
465                 470                 475                 480

Ile Glu Lys Thr Ile Ser Lys Ala Lys Gly Gln Pro Arg Glu Pro Gln
                485                 490                 495

Val Tyr Thr Leu Pro Pro Ser Arg Asp Glu Leu Thr Lys Asn Gln Val
            500                 505                 510

Ser Leu Thr Cys Leu Val Lys Gly Phe Tyr Pro Ser Asp Ile Ala Val
        515                 520                 525

Glu Trp Glu Ser Asn Gly Gln Pro Glu Asn Asn Tyr Lys Ala Thr Pro
    530                 535                 540

Pro Val Leu Asp Ser Asp Gly Ser Phe Phe Leu Tyr Ser Lys Leu Thr
545                 550                 555                 560

Val Asp Lys Ser Arg Trp Gln Gln Gly Asn Val Phe Ser Cys Ser Val
                565                 570                 575

Met His Glu Ala Leu His Asn His Tyr Thr Gln Lys Ser Leu Ser Leu
            580                 585                 590

Ser Pro Gly Lys
        595

<210> SEQ ID NO 10
<211> LENGTH: 10
<212> TYPE: PRT
<213> ORGANISM: Artificial Sequence
<220> FEATURE:
<223> OTHER INFORMATION: N-terminus of fusion protein.

<400> SEQUENCE: 10

Gln Cys Lys Ile Leu Arg Cys Asn Ala Glu
1               5                   10
```

-continued

```
<210> SEQ ID NO 11
<211> LENGTH: 5638
<212> TYPE: DNA
<213> ORGANISM: Artificial Sequence
<220> FEATURE:
<223> OTHER INFORMATION: Encodes HJV.Fc fusion.

<400> SEQUENCE: 11
```

| | | | | | |
|---|---|---|---|---|---|
| ttctagagaa | tccagacatg | ataagataca | ttgatgagtt | tggacaaacc | acaactagaa | 60 |
| tgcagtgaaa | aaaatgcttt | atttgtgaaa | tttgtgatgc | tattgcttta | tttgtaacca | 120 |
| ttataagctg | caataaacaa | gttaacaaca | acaattgcat | tcattttatg | tttcaggttc | 180 |
| aggggggaggt | gtgggaggtt | ttttaaagca | agtaaaacct | ctacaaatgt | ggtatggctg | 240 |
| attatgatca | atcgatgtcg | accaattcgt | aatcatgtca | tagctgtttc | ctgtgtgaaa | 300 |
| ttgttatccg | ctcacaattc | cacacaacat | acgagccgga | agcataaagt | gtaaagcctg | 360 |
| gggtgcctaa | tgagtgagct | aactcacatt | aattgcgttg | cgctcactgc | ccgctttcca | 420 |
| gtcgggaaac | ctgtcgtgcc | agctgcatta | atgaatcggc | caacgcgcgg | ggagaggcgg | 480 |
| tttgcgtatt | gggcgctctt | ccgcttcctc | gctcactgac | tcgctgcgct | cggtcgttcg | 540 |
| gctgcggcga | gcggtatcag | ctcactcaaa | ggcggtaata | cggttatcca | cagaatcagg | 600 |
| ggataacgca | ggaaagaaca | tgtgagcaaa | aggccagcaa | aaggccagga | accgtaaaaa | 660 |
| ggccgcgttg | ctggcgtttt | tccataggct | ccgcccccct | gacgagcatc | acaaaaatcg | 720 |
| acgctcaagt | cagaggtggc | gaaacccgac | aggactataa | agataccagg | cgtttccccc | 780 |
| tggaagctcc | ctcgtgcgct | ctcctgttcc | gaccctgccg | cttaccggat | acctgtccgc | 840 |
| ctttctccct | tcgggaagcg | tggcgctttc | tcatagctca | cgctgtaggt | atctcagttc | 900 |
| ggtgtaggtc | gttcgctcca | agctgggctg | tgagcacgaa | ccccccgttc | agcccgaccg | 960 |
| ctgcgcctta | tccggtaact | atcgtcttga | gtccaacccg | gtaagacacg | acttatcgcc | 1020 |
| actggcagca | gccactggta | acaggattag | cagagcgagg | tatgtaggcg | gtgctacaga | 1080 |
| gttcttgaag | tggtggccta | actacggcta | cactagaaga | acagtatttg | gtatctgcgc | 1140 |
| tctgctgaag | ccagttacct | tcggaaaaag | agttggtagc | tcttgatccg | gcaaacaaac | 1200 |
| caccgctggt | agcggtggtt | ttttgtttg | caagcagcag | attacgcgca | gaaaaaaagg | 1260 |
| atctcaagaa | gatcctttga | tcttttctac | ggggtctgac | gctcagtgga | acgaaaactc | 1320 |
| acgttaaggg | attttggtca | tgagattatc | aaaaaggatc | ttcacctaga | tccttttaaa | 1380 |
| ttaaaaatga | agttttaaat | caatctaaag | tatatatgag | taaacttggt | ctgacagtta | 1440 |
| ccaatgctta | atcagtgagg | cacctatctc | agcgatctgt | ctatttcgtt | catccatagt | 1500 |
| tgcctgactc | cccgtcgtgt | agataactac | gatacgggag | ggcttaccat | ctggccccag | 1560 |
| tgctgcaatg | ataccgcgag | acccacgctc | accggctcca | gatttatcag | caataaacca | 1620 |
| gccagccgga | agggccgagc | gcagaagtgg | tcctgcaact | ttatccgcct | ccatccagtc | 1680 |
| tattaattgt | tgccgggaag | ctagagtaag | tagttcgcca | gttaatagtt | tgcgcaacgt | 1740 |
| tgttgccatt | gctacaggca | tcgtggtgtc | acgctcgtcg | tttggtatgg | cttcattcag | 1800 |
| ctccggttcc | caacgatcaa | ggcgagttac | atgatccccc | atgttgtgca | aaaaagcggt | 1860 |
| tagctccttc | ggtcctccga | tcgttgtcag | aagtaagttg | gccgcagtgt | tatcactcat | 1920 |
| ggttatggca | gcactgcata | attctcttac | tgtcatgcca | tccgtaagat | gcttttctgt | 1980 |
| gactggtgag | tactcaacca | agtcattctg | agaatagtgt | atgcggcgac | cgagttgctc | 2040 |
| ttgcccggcg | tcaatacggg | ataataccgc | gccacatagc | agaactttaa | aagtgctcat | 2100 |

```
cattggaaaa cgttcttcgg ggcgaaaact ctcaaggatc ttaccgctgt tgagatccag    2160
ttcgatgtaa cccactcgcg cacccaactg atcttcagca tcttttactt tcaccagcgt    2220
ttctgggtga gcaaaaacag gaaggcaaaa tgccgcaaaa aagggaataa gggcgacacg    2280
gaaatgttga atactcatac tcttcctttt tcaatattat tgaagcattt atcagggtta    2340
ttgtctcatg agcggataca tatttgaatg tatttagaaa aataaacaaa tagggggttcc   2400 gcgcacattt ccccgaaaag tgccacctga cgtctaagaa accattatta tcatgacatt    2460
aacctataaa aataggcgta tcacgaggcc ctttcgtctc gcgcgtttcg gtgatgacgg    2520
tgaaaacctc tgacacatgc agctcccgga gacggtcaca gcttgtctgt aagcggatgc    2580
cgggagcaga caagcccgtc agggcgcgtc agcgggtgtt ggcgggtgtc ggggctggct    2640
taactatgcg gcatcagagc agattgtact gagagcgcac catatgcggt gtgaaatacc    2700
gcacagatgc gtaaggagaa aataccgcat caggcgccat tcgccattca ggctgcgcaa    2760
ctgttgggaa gggcgatcgg tgcgggcctc ttcgctatta cgccagctgg cgaaaggggg    2820
atgtgctgca aggcgattaa gttgggtaac gccagggttt tcccagtcac gacgttgtaa    2880
aacgacggcc agtgccaagc tagcggccgc cacgagtcta gctagagtac gaattcgagc    2940
tcggaacccc tatacattga atcaatattg gcaattagcc atattagtca ttggttatat    3000
agcataaatc aatattggct attggccatt gcatacgttg tatctatatc ataatatgta    3060
catttatatt ggctcatgtc caatatgacc gccatgttga cattgattat tgactagtta    3120
ttaatagtaa tcaattacgg ggtcattagt tcatagccca tatatggagt tccgcgttac    3180
ataacttacg gtaaatggcc cgcctggctg accgcccaac gacccccgcc cattgacgtc    3240
aataatgacg tatgttccca tagtaacgcc aatagggact ttccattgac gtcaatgggt    3300
ggagtattta cggtaaactg cccacttggc agtacatcaa gtgtatcata tgccaagtcc    3360
gccccctatt gacgtcaatg acggtaaatg gcccgcctgg cattatgccc agtacatgac    3420
cttacgggac tttcctactt ggcagtacat ctacgtatta gtcatcgcta ttaccatggt    3480
gatgcggttt tggcagtaca ccaatgggcg tggatagcgg tttgactcac ggggatttcc    3540
aagtctccac cccattgacg tcaatgggag tttgttttgg caccaaaatc aacgggactt    3600
tccaaaatgt cgtaataacc ccgccccgtt gacgcaaatg ggcggtaggc gtgtacggtg    3660
ggaggtctat ataagcagag ctcgtttagt gaaccgtcag atcggggatc cgatatccac    3720
catgggggag ccaggccagt cccctagtcc caggtcctcc catggcagtc cccaactct    3780 aagcactctc actctcctgc tgctcctctg tggacatgct cattctcaat gcaagatcct    3840
ccgctgcaat gctgagtacg tatcgtccac tctgagcctt agaggtgggg gttcatcagg    3900
agcacttcga ggaggaggag gaggaggccg gggtggaggg gtgggctctg gcggcctctg    3960
tcgagccctc cgctcctatg cgctctgcac tcggcgcacc gcccgcacct gccgcgggga    4020
cctcgccttc cattcggcgg tacatggcat cgaagacctg atgatccagc acaactgctc    4080
ccgccagggc cctacagccc ctccccgcc ccggggcccc gccttccag gcgcgggctc     4140 cggcctccct gccccggacc cttgtgacta tgaaggccgg ttttcccggc tgcatggtcg    4200
tcccccgggg ttcttgcatt gcgcttcctt cgggggaccc catgtgcgca gcttccacca    4260
tcactttcac acatgccgtg tccaaggagc ttggcctcta ctggataatg acttcctctt    4320
tgtccaagcc accagctccc ccatggcgtt gggggccaac gctaccgcca cccggaagct    4380
caccatcata tttaagaaca tgcaggaatg cattgatcag aaggtgtatc aggctgaggt    4440
ggataatctt cctgtagcct ttgaagatgg ttctatcaat ggaggtgacc gacctgggg     4500
```

-continued

```
atccagtttg tcgattcaaa ctgctaaccc tgggaaccat gtggagatcc aagctgccta    4560
cattggcaca actataatca ttcggcagac agctgggcag ctctccttct ccatcaaggt    4620
agcagaggat gtggccatgg ccttctcagc tgaacaggac ctgcagctct gtgttggggg    4680
gtgccctcca agtcagcgac tctctcgatc agagcgcaat cgtcggggag ctataaccat    4740
tgatactgcc agacggctgt gcaaggaagg gcttccagtg gaagatgctt acttccattc    4800
ctgtgtcttt gatgttttaa tttctggtga tcccaacttt accgtggcag ctcaggcagc    4860
actggaggat gcccgagcct tcctgccaga cttagagaag ctgcatctct tccccctcagg   4920 tggtggtggt ggtgatccca aatcttgtga caaacctcac acatgcccac tgtgcccagc    4980
acctgaactc ctgggggac cgtcagtctt cctcttcccc ccaaaaccca aggacaccct     5040
catgatctcc cggaccctg aggtcacatg cgtggtggtg gacgtgagcc acgaagaccc    5100
tgaggtcaag ttcaactggt acgtggacgg cgtggaggtg cataatgcca agacaaagcc    5160
gcgggaggag cagtacaaca gcacgtaccg tgtggtcagc gtcctcaccg tcctgcacca    5220
ggactggctg aatggcaagg agtacaagtg caaggtctcc aacaaagccc tcccagcccc    5280
catcgagaaa accatctcca aagccaaagg gcagccccga gaaccacagg tgtacaccct    5340
gcccccatcc cgggatgagc tgaccaagaa ccaggtcagc ctgacctgcc tagtcaaagg    5400
cttctatccc agcgacatcg ccgtggagtg ggagagcaat gggcagccgg agaacaacta    5460
caaggccacg cctcccgtgc tggactccga cggctccttc ttcctctaca gcaagctcac    5520
cgtggacaag agcaggtggc agcagggaa cgtcttctca tgctccgtga tgcatgaggc    5580
tctgcacaac cactacacgc agaagagcct ctccctgtct ccgggtaaat gagctgat      5638
```